(12) United States Patent
Delenstarr

(10) Patent No.: US 7,608,396 B2
(45) Date of Patent: *Oct. 27, 2009

(54) SYSTEMS, TOOLS AND METHODS OF ASSAYING BIOLOGICAL MATERIALS USING SPATIALLY-ADDRESSABLE ARRAYS

(75) Inventor: Glenda C. Delenstarr, Belmont, CA (US)

(73) Assignee: Agilent Technologies, Santa Clara, CA (US)

( * ) Notice: Subject to any disclaimer, the term of this patent is extended or adjusted under 35 U.S.C. 154(b) by 232 days.

This patent is subject to a terminal disclaimer.

(21) Appl. No.: 11/400,717

(22) Filed: Apr. 6, 2006

(65) Prior Publication Data

US 2006/0246494 A1 Nov. 2, 2006

Related U.S. Application Data

(60) Continuation of application No. 10/193,777, filed on Jul. 11, 2002, now Pat. No. 7,052,841, which is a division of application No. 09/436,437, filed on Nov. 8, 1999, now Pat. No. 6,428,957.

(51) Int. Cl.
*C12Q 1/68* (2006.01)
*C07H 21/02* (2006.01)
*C07H 21/04* (2006.01)

(52) U.S. Cl. ............... 435/6; 536/23.1; 536/24.3; 536/24.33

(58) Field of Classification Search ............... None
See application file for complete search history.

(56) References Cited

U.S. PATENT DOCUMENTS

| | | | |
|---|---|---|---|
| 4,716,106 A | 12/1987 | Chiswell | |
| 4,731,325 A | 3/1988 | Palva et al. | |
| 4,751,177 A | 6/1988 | Stabinsky | |
| 4,868,105 A | 9/1989 | Urdea et al. | |
| 4,894,325 A | 1/1990 | Englehardt et al. | |
| 5,194,599 A | 3/1993 | Froehler | |
| 5,200,314 A | 4/1993 | Urdea | |
| 5,399,676 A | 3/1995 | Froehler | |
| 5,437,976 A | 8/1995 | Utermohlen | |
| 5,527,899 A | 6/1996 | Froehler | |
| 5,556,749 A | 9/1996 | Mitsuhashi et al. | |
| 5,604,097 A | 2/1997 | Brenner | |
| 5,635,352 A | 6/1997 | Urdea et al. | |
| 5,635,400 A | 6/1997 | Brenner | |
| 5,663,318 A | 9/1997 | Pegg et al. | |
| 5,681,697 A | 10/1997 | Urdea et al. | |
| 5,681,702 A | 10/1997 | Collins et al. | |
| 5,721,218 A | 2/1998 | Froehler | |
| 5,780,610 A | 7/1998 | Collins et al. | |
| 5,800,992 A * | 9/1998 | Fodor et al. | ............... 506/9 |
| 5,846,719 A | 12/1998 | Brenner et al. | |
| 5,858,671 A | 1/1999 | Jones | |
| 5,871,902 A | 2/1999 | Weininger et al. | |
| 5,922,617 A | 7/1999 | Wang et al. | |
| 6,083,763 A | 7/2000 | Balch | |
| 6,110,678 A | 8/2000 | Weisburg et al. | |
| 6,185,561 B1 | 2/2001 | Balaban et al. | |
| 6,232,066 B1 | 5/2001 | Felder et al. | |
| 7,052,841 B2 * | 5/2006 | Delenstarr | ............... 435/6 |

FOREIGN PATENT DOCUMENTS

| | | |
|---|---|---|
| EP | 0 799 897 A1 | 10/1997 |
| WO | WO 96/41011 | 12/1996 |
| WO | WO 97/31256 | 8/1997 |

OTHER PUBLICATIONS

Daniel D. Shoemaker, et al., "Quantitative Phenotypic Analysis of Yeast Deletion Mutants Using A Highly Parallel Molecular Bar-Coding Strategy", *Nature Genetics*, vol. 14, pp. 450-456, Dec. 1996.
M. Koga, et al., "Alternating α, β- Oligothymidylates with Alternating (3'→3')- and (5'→5')- Internucleotidic Phosphodiester Linkages as Models for Antisense Oligodeoxyribonucleotides", *The Journal of Organic Chemistry*, vol. 56, No. 12, Jun. 7, 1991, pp. 3757-3759.
M. Koga, et al., "The synthesis of alternating α, β- oligodeoxyribonucleotides with alternating (3'→3')- and (5'→5')- internucleotic linkages as potential therapeutic agents", *Nucleic Acids Symposium Series*, No. 29, pp. 3-4 (1993).
M. Koga, et al., "Synthesis and Physicochemical Properties of Alternating (3'→3')- and (5'→5')- Internucleotidic Phosphodiester Linkages", *J. Org. Chem.* 1995, 60, 1520-1530.

* cited by examiner

*Primary Examiner*—Young J Kim

(57) ABSTRACT

Systems, tools and methods are used to perform complex sandwich hybridization assays of biological material. The tools comprise biological solution probes having a first region for hybridizing to capture probes on a universal assay apparatus, and a second region for hybridizing to a sample target. The solution probe assembles the target to the apparatus by hybridizing the second region to the target and the first region to the capture probe. Multiple biological samples, having a plurality of targets per sample, can be multiplexed on the same universal array. The customized solution probe addresses and assembles a predetermined target-sample combination onto the array at a corresponding capture probe address location. Specificity and sensitivity of the assay are provided by the incorporation of a modified monomer in the capture probe and a similarly modified monomer complement in the first region of the solution probe. The modified monomers preferentially hybridize with each other.

11 Claims, 13 Drawing Sheets

SYSTEMS, TOOLS AND METHODS OF ASSAYING BIOLOGICAL MATERIALS USING SPATIALLY-ADDRESSABLE ARRAYS

This is a Continuation Application of Ser. No. 10/193,777, filed Jul. 11, 2002, that issued as U.S. Pat. No. 7,052,841 on May 30, 2006, which is a Divisional Application of parent Application Ser. No. 09/436,437, filed on Nov. 8, 1999, that issued as U.S. Pat. No. 6,428,957 on Aug. 6, 2002, the entire disclosures of which are incorporated herein by reference.

TECHNICAL FIELD

This invention relates to analytical tools and methods for monitoring levels of gene expression and mutations in gene sequences. In particular, the invention relates to assay systems, tools and methods with enhanced specificity and sensitivity that are capable of multiplexing one or more sample (s), having one or more target material(s) per sample, on a single array.

BACKGROUND ART

Conventional analysis of biological materials, such as DNA, RNA, proteins, antibodies, ligands and the like, employs a basic hybridization assay which comprises a substrate or support having biological material chemically bound thereto. The biological material may be either biological "probes" of known molecular make-up or "targets" having an unknown characteristic to be determined. For the purposes of simplicity, hereinafter the material bound to the substrate will be referred to as probes. The probes are hybridized with a target sample and the hybridization results are analyzed. The hybridization results reveal information about the targets based on what is known about the probes. The surface bound probes are typically formed of DNA oligonucleotides, cDNA's, PCR products, proteins, antibodies, antigens, receptors, ligands, and the like, that are complementary to the biological target material under test.

Another conventional assay is the sandwich hybridization assay. Sandwich hybridization assays use probes designed with a sequence region that is complementary to the target under test and a separate sequence region or a separate binding partner that is complementary to a sequence, or specific to a binding partner, on a support. The probes are hybridized with the target sample and with its complement on the support in a two step process. Variations on this basic scheme have been developed to enhance accuracy, facilitate separation of duplexes and amplify signals for detection during analysis (see for example, U.S. Pat. Nos. 4,868,105; 5,200,314; 5,635, 352; and 5,681,697, issued to Urdea (or Urdea et al.) and U.S. Pat. Nos. 5,681,702 and 5,780,610, both issued to Collins et al.).

However, a drawback to the sandwich hybridization technique is cross hybridization. For example, if the target material hybridizes to the wrong region of the probe, then the probe does not hybridize with its appropriate complement on the support. This may yield a false negative result. Conversely, if the target material hybridizes incorrectly to the sequence on the support, a false positive result may occur. Thus, information about the target material becomes less accurate. There has been much effort in developing methods for minimizing cross-hybridization in sandwich hybridization assays.

U.S. Pat. No. 5,604,097, U.S. Pat. No. 5,635,400 and U.S. Pat. No. 5,846,719, issued to S. Brenner and Brenner et al., respectively (hereinafter "Brenner"), disclose methods of sorting polynucleotides in basic hybridization assays using 'minimally cross-hybridization' sets of oligonucleotide tags. Brenner is silent on using the methods of sorting for sandwich hybridization assays. Oligonucleotide tags from the set of tags are attached to a sample of polynucleotides under test. The polynucleotides with oligonucleotide tags attached are immobilized on a solid phase support by hybridizing the tags to a complementary sequence on the support.

Brenner discloses a general algorithm and computer program for computing minimally cross-hybridizing sets of tags and complements. Brenner's test for "minimally cross-hybridizing" is based upon the conventional technique of symbolic matching of sequences. Although useful in some cases, the conventional symbolic matching technique has drawbacks that affect the technique's ability to effectively discriminate against cross-hybridizations. Since some base mismatches are much less destabilizing to the duplex Tm than other mismatches, the method of Brenner is capable of generating mismatch sequences which are actually capable of cross-hybridizing. The conventional method and the method disclosed by Brenner do not take in account cross-hybridizing mismatches. In addition, Brenner does not teach a method for protecting against the formation of intramolecular structures. These structures, such as hairpins, will inhibit the correct duplex formation between tags and their complements. If cross-hybridizing mismatches and intramolecular structures were screenable according to Brenner's method, the number of tags and complement sets after such screening, which would actually qualify as "minimally cross-hybridizing", would be greatly reduced. With state-of-the-art arrays containing more than 10,000 features, the tag sets disclosed by Brenner would have to have longer lengths than that disclosed by Brenner in order to yield a high enough number to accommodate such an array. However, longer length tags and complements are more expensive to synthesize.

Thus, it would be advantageous to have a large number of 'tag and complement' sets, for example, for use in diagnostic assays of biological materials, wherein the tag and complement lengths are as short as possible to save on cost. Further, it would be advantageous if the specificity between the tags and their complements was increased to avoid or minimize cross-hybridizations and still further if the sensitivity between the tags and their complements was increased by decreasing the probability of intramolecular structures, such as hairpins, within the sequences. Still further, it would be advantageous if such tag and complement sets could be adapted to sandwich hybridization assays using arrays of over 10,000 features.

U.S. Pat. No. 5,399 676, U.S. Pat. No. 5,527,899, and U.S. Pat. No. 5,721,218 issued to B. Froehler, disclose using oligonucleotides with "inverted polarity" for forming anti-sense probes having an extended triple helix with a double-helical nucleotide duplex. The anti-sense probes are used in clinical intervention applications to decrease specific RNA translation. Froehler discloses that the inverted polarity oligonucleotides can skip from one complementary strand in the duplex to the other as its polarity shifts. Such inverted polarity also stabilizes the single-stranded oligonucleotides to exonuclease degradation. However, Froehler is silent on using inverted polarity oligonucleotides for minimizing cross hybridization in diagnostic assays. In addition, Froehler discloses using probes that actually have specific intramolecular structures, which is consistent with the use of anti-sense probes in clinical intervention applications.

Thus, it would be advantageous to have tools and methods for diagnostically assaying one or more biological sample(s), having one or more target(s) per sample, on a single array, using sandwich hybridization assay techniques. In addition, it would be advantageous for the tools and methods to have increased specificity between complementary probe sequences to minimize the likelihood of cross-hybridization between biological materials in a systematic fashion. Moreover, it would be advantageous for such tools and methods to have increased sensitivity between complementary probe sequences to minimize the likelihood of intramolecular structures within the probes. The increased specificity and sensitivity of such tools and methods would increase the accuracy and usefulness of sandwich. hybridization assays, especially on an array.

SUMMARY OF THE INVENTION

The present invention provides sandwich hybridization assay systems, biological tools and methods of diagnostically assaying biological materials. The present invention is particularly useful for sandwich hybridization assays on arrays and provides an addressable, self-assembling array. The systems, tools and methods are capable of multiplexing one or more sample(s), having one or more target(s) per sample on a single array. Moreover, the systems, tools and methods of the invention have good specificity by systematically providing a reduced likelihood of cross-hybridizations from occurring, and good sensitivity by systematically providing a reduced likelihood of intramolecular structures from forming. The sandwich hybridization assay systems, tools and methods of the present invention provide powerful means for sorting, tracking, identifying, and determining other characteristics of biological target compounds for diagnostic applications.

According to one aspect of the present invention, an assay system for multiplexing on a single array one or more biological sample(s), having one or more biological target(s) per sample, is provided. The assay system for multiplexing comprises an array apparatus that has a first plurality of biological probes, called capture probes, in an array pattern of features on a substrate. Each capture probe in each feature location is different from the others in the first plurality. Each different capture probe is a different address on the array apparatus.

The assay system for multiplexing still further comprises a second plurality of biological probes, called solution probes. Each solution probe comprises a first region and a second region. Each solution probe is different from others in the second plurality by comprising a different first region, and may comprise a different second region, depending on the assay. The first region of each solution probe is complementary to a respective capture probe on the array. The second region of the solution probe is complementary to a respective biological target in a sample. Thus, the solution probes essentially assemble or deliver different biological target-and-biological sample combinations being assayed on the array corresponding to the addresses of the different first probes. The presence, quantity and/or other features of particular targets in particular samples are ascertainable depending on whether the particular target-sample combinations have been assembled to their respective capture probe location on the array during the assay.

According to another aspect of the present invention, an assay method of multiplexing on a single array one or more biological sample(s), having one or more biological target(s) per sample, is provided. The assay method of multiplexing comprises the step of providing an array apparatus that has a first plurality of biological probes, called capture probes, in an array pattern of features on a substrate. Each capture probe of the first plurality is different and each different capture probe is located in a different feature location of the array. Each different capture probe is an address on the array apparatus.

The assay method of multiplexing further comprises the step of providing a second plurality of biological probes, called solution probes. Each solution probe of the second plurality has a first region and a second region. Each solution probe is different from other of the second plurality by having a different first region. Each different first region is complementary to a different capture probe on the array. The second region is complementary to a biological target from a biological sample, and therefore, the second region may be the same or different on each solution probe of the second plurality, depending on the assay to be performed. As mentioned above for the system, the solution probes essentially assemble or deliver the different biological target-and-biological sample combinations being assayed on the array corresponding to the addresses of the different capture probes. The assay method of multiplexing still further comprises the steps of assembling the biological target(s) from the sample(s) to the array, and removing unassembled biological materials from the array and analyzing the assay results using conventional methods. The presence of the biological target(s) from respective biological sample(s) at corresponding capture probe feature locations on the array indicates, among other things, whether and how much of particular biological targets exist in particular biological samples.

During the step of assembling, a target from a sample will hybridize with a complementary second region of a solution probe and the first region of this solution probe will hybridize with a complementary capture probe on the array corresponding to the target-sample combination. The solution probes of the system essentially assemble or "address" the targets to the array in a predetermined (pre-addressed) fashion during the assay. The assay system and method for multiplexing of the present invention advantageously provide an assay that is self-assembling and addressable, and capable of sorting for evaluation purposes: one target from a plurality of different samples (or patients), a plurality of different targets from one sample (patient), or a plurality of different targets from a plurality of different samples on the same array. The hybridizations may be performed simultaneous or preferably, in a two step hybridization process.

According to still another aspect of the present invention, a set of biological probes used in a sandwich hybridization assay of a biological target on an array of biological features is provided. The set of biological probes comprises a plurality of individual solution probes that each comprises a first probe region, called an anti-capture region, complementary to a biological feature on the array. Each individual solution probe further comprises a second probe region that is complementary to the biological target being assayed. Each solution probe in a particular set is different by comprising a different anti-capture region. The anti-target region on each different solution probe of a set may be the same or different depending on the type of assay being performed. Moreover, there may be multiple copies of each different solution probe in the set. There is a different set of biological probes for each type of biological material being assayed (e.g., nucleic acids, proteins, sugars, etc.).

Thus, each solution probe of a particular set may comprise first regions selected from oligonucleotides, antibodies, antigens, ligands and receptors, for example, depending on the biological make-up of the biological features on the array. Further, the second regions of this particular set may comprise second regions selected from cDNA, PCR products, oligonucleotides, antibodies, antigens, ligands and receptors, for example, depending on the biological make-up of the biological targets to be assayed. For example, each solution probe of a particular set may comprise a different antigen linked to the same or a different cDNA, wherein the different antigens are complementary to a plurality of different antibody features on an array and the cDNA is complementary to oligonucleotide (e.g., mRNA) target material(s) to be assayed. Thus, each set of solution probes is customized to a particular assay. The generic set of capture probes on the universal array apparatus provides "addresses" corresponding to the location of the capture probes on the array where target material being assayed is to be delivered and the set of solution probes essentially delivers the target material to its respective address during the assay. The set of biological probes are particularly useful for multiplexing assays of one or more biological sample(s), having one or more biological target(s) per sample, on a single array.

In still another aspect of the present invention, a system for assaying biological materials having specificity and sensitivity is provided. The system comprises an apparatus that has a first set of biological material probes, called capture probes, on a substrate. Each capture probe of the set comprises a sequence of monomers. Each set of capture probes is generic to the biological material to be tested. Each capture probe in the set may be different by having a different sequence of monomers. There may be multiple copies of each different capture probe in the set.

The system having specificity and sensitivity further comprises a second set of biological material probes, called solution probes. There is a different set of solution probes for each type of biological material being tested. Each solution probe of the set comprises a first sequence region, called an anti-capture sequence, that is complementary to the monomers in the capture probe sequence for hybridizing or binding to the capture probe, and a second region, called an anti-target region, for hybridizing or binding to the target. Each solution probe in a particular set may be different by comprising a different anti-capture sequence. Further, each solution probe may comprise the same or different anti-target region depending on the biological materials to be assayed. There may be multiple copies of each different solution probe in the set. The set of solution probes assembles the target material to be tested to the assay substrate by hybridizing the second region to the target and hybridizing the first region to the capture probes on the substrate. The hybridizations may be performed simultaneously or preferably, in two hybridization steps.

In accordance with this aspect of the invention, the capture probes and the anti-capture sequences on the solution probes each comprise a complementary chemically modified monomer that preferentially hybridize or bind to each other instead of to a complementary unmodified (or not similarly modified) monomer. The preference of the modified monomers of the present invention provides specificity and sensitivity to the system. The system is specific because the chemically modified monomer in the anti-capture sequences will preferentially hybridize or bind with the complementary similarly modified monomer in the respective capture probe, and likewise the modified monomer in the capture probe will preferentially hybridize or bind with the similarly modified monomer in the complementary anti-capture sequence. Thus, cross-hybridizations (i.e., hybridizations with mismatches) are less likely to occur. The system is sensitive because the chemically modified monomers in the capture probes and anti-capture sequences are less likely to hybridize to complementary unmodified (or not similarly modified) monomers or to noncomplementary monomers present in the capture probes, solution probes or target sequences. Thus, hybridizations that cause intramolecular structures within the capture probes or within the anti-capture sequences are less likely to occur.

In yet another aspect of the present invention, a method of assaying biological materials having specificity and sensitivity is provided. The method comprises the step of providing an apparatus having a first set of biological probes, called capture probes, comprising a sequence of monomers, on a substrate.

The method having specificity and sensitivity further comprises the step of providing a second set of biological probes, called solution probes. There is a different set of solution probes for each type of biological material to be tested. Each solution probe of the set comprises a first sequence region of monomers, called an anti-capture sequence region, and a second region, called an anti-target region. The anti-capture sequence region of each solution probe is complementary to the monomer sequence of a capture probe in the set, and the anti-target region on the solution probe is complementary to a biological target to be assayed.

The complementary capture probes and anti-capture monomer sequences each include a complementary chemically modified monomer that prefers to hybridize or bind to each other instead of to a complementary monomer that is not similarly modified.

The method of assaying biological materials having specificity and sensitivity further comprises the step of assembling the target material to the substrate for evaluation. During the step of assembling, the set of solution probes is incubated with a target biological material to cause hybridization or binding between targets and respective complementary anti-target regions of the solution probes. Further, the set of solution probes is incubated with the set of capture probes on the assay apparatus to cause hybridization or binding between complementary capture sequences and anti-capture sequences of the solution probes. It is during the step of assembling that the complementary chemically modified monomers on the capture probes and anti-capture sequences preferentially hybridize to each other. The hybridizations may be performed simultaneously or preferably, in two hybridization steps. After hybridization, the incubated substrate is washed to remove unhybridized/unbound material and the results of the assay are analyzed, according to conventional methods.

In a preferred embodiment, the capture probe and anti-capture sequences are oligonucleotides and the chemically modified monomers in the capture probes and anti-capture sequences are reversed polarity nucleotides relative to the polarity of the nucleotides of the respective sequence. The anti-capture sequence, having a nucleotide with reversed polarity, is complementary to the nucleotide with reversed polarity on the capture probe. The complementary reversed polarity nucleotides prefer to hybridize to each other because they form a thermodynamically more stable hybridization than a hybridization between a reversed polarity nucleotide and its complementary nucleotide whose polarity is not similarly reversed.

The chemical modification introduced into the probes of the system and method essentially improves the likelihood that the appropriate or intended capture probes and solution probes will specifically and sensitively hybridize or bind together. Advantageously, the system and method of assaying essentially systematically provide a reduced likelihood of cross-hybridizations between the capture probes and sequences that are not complementary to the capture probes, such as non-complementary anti-capture sequences of the solution probes, anti-target regions of solution probes, or target sequences. Further, the system and method having specificity and sensitivity essentially systematically provide a reduced likelihood of cross-hybridization between anti-capture sequences of the solution probes and sequences that are not complementary to the anti-capture sequences, such as non-complementary capture sequences on the array, other anti-capture sequences, anti-target sequences of solution probes, or target sequences. In addition, the system and method having specificity and sensitivity essentially systematically provide a reduced likelihood of any undesirable formation of intramolecular structures within the capture probes and anti-capture sequences of the invention. The system and method have a reduced likelihood of cross-hybridizations and intramolecular structures because the probes comprise modified monomers that prefer to hybridize to each other rather than to a complementary unmodified (or not similarly modified) monomer.

The system and method having specificity and sensitivity are useful in sandwich hybridization assays, sandwich hybridization assays using arrays, and in particular, in the system and method described above for multiplexing one or more biological sample(s), having one or more target(s) per sample on a single array. When used in multiplexing array assay applications, the system and method having specificity and sensitivity advantageously provide assays with specific and sensitive addressing and self-assembling capabilities.

The system and method having specificity and sensitivity of the invention uses both chemically modified monomers and monomers that are not modified (or not modified in a similar fashion to the chemically modified monomers of the invention), in the same capture probes and anti-capture sequences. Using both chemically modified monomers and not similarly modified monomers increases the number of different monomers ("letters") available with which to make new sequences ("words") for the capture probes and anti-capture sequences of the invention. Thus, a larger number of different capture probe sequences and their complementary anti-capture sequences are readily and systematically generated by the present invention that are specific and sensitive compared to conventional assays.

In the preferred embodiment of oligonucleotide capture probes and anti-capture sequence regions of the solution probes of the system and method having specificity and sensitivity, there are at least eight nucleotides (four with one polarity and four counterparts with respectively reversed polarity) from which to form the complementary capture probe and anti-capture region sequences. Therefore, a much larger set of probes and anti-capture sequences with specificity and sensitivity are provided. Moreover, the specificity that the complementary reversed polarity nucleotides have for each other allows the length of the capture probes and anti-capture regions to be shorter than conventional probes to save on cost.

The system and method having specificity and sensitivity advantageously provide a set of greater than 10,000 probes, which are unique with respect to each other. Mammalian genomes are estimated to contain over 10,000 expressed genes. With multiple splicing variants, the number of probes needed to sample the expressed genes is even higher. Thus, if one wanted to assay for all of the expressed genes and variants on the same array, one would need in excess of 10,000 biological capture features on the array. The system and method having specificity and sensitivity provide this capability.

In another aspect of the present invention, a kit is provided that comprises the assay apparatus of capture probes and the set of solution probes packaged with written instructions for use in accordance with one or more assay methods of the present invention. The kit can be provided to users, such as diagnostic, research and/or analytical laboratories. The kit can comprise either (i) the array apparatus of capture probes and set of solution probes for multiplexing sandwich assays on arrays, or (ii) the apparatus of capture probes and a set of solution probes for sandwich assays having specificity and sensitivity, or (iii) a combination of both, comprising the array apparatus of capture probes and the set of solution probes having specificity and sensitivity for multiplexing sandwich assays, in accordance with one or more embodiments of the invention.

Moreover, the systems, tools and methods of the present invention also provide cost effective custom assays. Customization of an assay resides in the preparation of the second set of probes (solution probes), rather than in the preparation of the first set of probes (capture probes) or the array apparatus of capture probes. Therefore, large numbers of generic or universal assay substrates with bound capture probes can be manufactured at a time, thereby saving in cost and turnaround time for custom orders. This is particular advantageous for large numbers of generic or universal array substrates of the invention. The second set of probes are prepared separately, as needed, or prepared in advance and stored separately in solution or dry, preferably frozen, until needed. The solution probes are customized to the biological materials of the generic or universal array apparatus and to the biological targets to be assayed.

BRIEF DESCRIPTION OF THE DRAWINGS

The various features and advantages of the present invention may be more readily understood with reference to the following detailed description taken in conjunction with the accompanying drawings, where like reference numerals designate like structural elements, and in which.

MODES FOR CARRYING OUT THE INVENTION

Definitions

Figure 1:
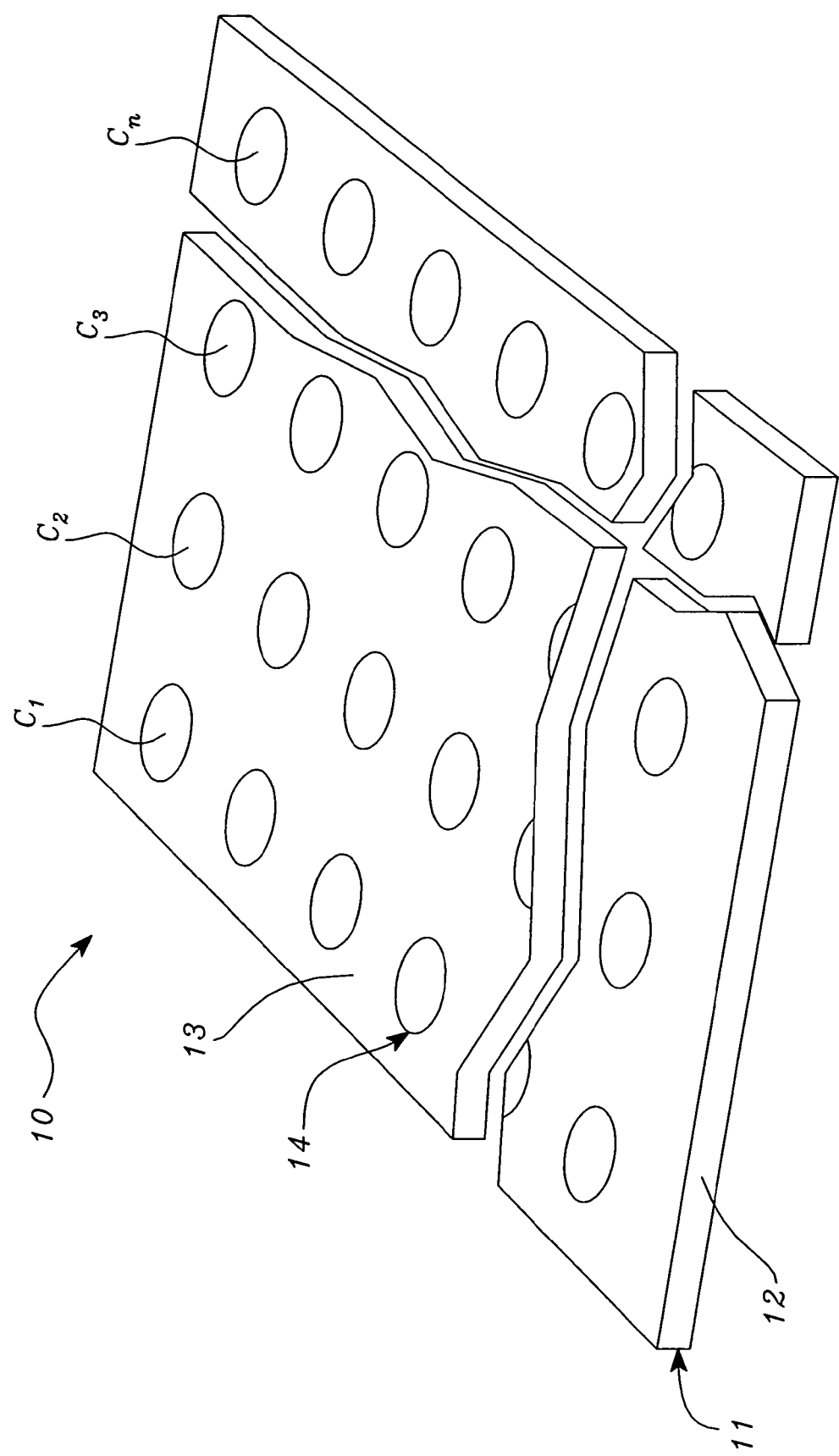
FIG. 1 is a perspective view of one embodiment of an apparatus of the present invention illustrating an array of capture probe feature locations on a substrate.

The following terms are intended to have the following general meanings as they are used herein:

Polynucleotide—a compound or composition that is a polymeric nucleotide or nucleic acid polymer. The polynucleotide may be a natural compound or a synthetic compound. In the context of an assay, the polynucleotide can have from about 5 to 5,000,000 or more nucleotides. The larger polynucleotides are generally found in the natural state. In an isolated state the polynucleotide can have about 30 to 50,000 or more nucleotides, usually about 100 to 20,000 nucleotides, more frequently 500 to 10,000 nucleotides. It is thus obvious that isolation of a polynucleotide from the natural state often results in fragmentation. The polynucleotides include nucleic acids, and fragments thereof, from any source in purified or unpurified form including DNA, double-stranded or single stranded (dsDNA and ssDNA), and RNA, including t-RNA, m-RNA, r-RNA, mitochondrial DNA and RNA, chloroplast DNA and RNA, DNA/RNA hybrids, or mixtures thereof, genes, chromosomes, plasmids, the genomes of biological materials such as microorganisms, e.g. bacteria, yeasts, viruses, viroids, molds, fungi, plants, animals, humans, and the like. The polynucleotide can be only a minor fraction of a complex mixture such as a biological sample. Also included are genes, such as hemoglobin gene for sickle-cell anemia, cystic fibrosis gene, oncogenes, cDNA, and the like.

Polynucleotides include analogs of naturally occurring polynucleotides in which one or more nucleotides are modified over naturally occurring nucleotides. Polynucleotides then, include compounds produced synthetically (for example, PNA as described in U.S. Pat. No. 5,948,902 and the references cited therein, all of which are incorporated herein by reference) which can hybridize in a sequence specific manner analogous to that of two naturally occurring polynucleotides.

The polynucleotide can be obtained from various biological materials by procedures well known in the art. The polynucleotide, where appropriate, may be cleaved to obtain a fragment that contains a target nucleotide sequence, for example, by shearing or by treatment with a restriction endonuclease or other site specific chemical cleavage method, such as limited RNase digestion, to produce smaller RNA fragments.

For purposes of this invention, the polynucleotide, or a cleaved fragment obtained from the polynucleotide, will usually be at least partially denatured or single stranded or treated to render it denatured or single stranded. Such treatments are well known in the art and include, for instance, heat or alkali treatment, or enzymatic digestion of one strand. For example, double stranded DNA (dsDNA) can be heated at 90-100° C. for a period of about 1 to 10 minutes to produce denatured material, while RNA produced via transcription from a dsDNA template is already single stranded.

Oligonucleotide—a polynucleotide, usually single stranded, usually a synthetic polynucleotide but may be a naturally occurring polynucleotide. The oligonucleotide(s) are usually comprised of a sequence of at least 5 nucleotides, usually, 10 to 100 nucleotides, more usually, 20 to 50 nucleotides, preferably, 10 to 30 nucleotides, more preferably, 20 to 30 nucleotides, and desirably about 25 nucleotides in length.

Various techniques can be employed for preparing an oligonucleotide. Such oligonucleotides can be obtained by biological synthesis or by chemical synthesis. For short sequences (up to about 100 nucleotides), chemical synthesis will frequently be more economical as compared to the biological synthesis. In addition to economy, chemical synthesis provides a convenient way of incorporating low molecular weight compounds and/or modified bases during specific synthesis steps. Furthermore, chemical synthesis is very flexible in the choice of length and region of target polynucleotides binding sequence. The oligonucleotide can be synthesized by standard methods such as those used in commercial automated nucleic acid synthesizers. Chemical synthesis of DNA on a suitably modified glass or resin can result in DNA covalently attached to the surface. This may offer advantages in washing and sample handling. For longer sequences standard replication methods employed in molecular biology can be used such as the use of M13 for single stranded DNA as described in J. Messing (1983) *Methods Enzymol.* 101:20-78.

In situ synthesis of oligonucleotide or polynucleotide probes on the substrate is performed in accordance with well-known chemical processes, including, but not limited to sequential addition of nucleotide phosphoramidites to surface-linked hydroxyl groups, as described by T. Brown and Dorcas J. S. Brown in *Oligonucleotides and Analogues A Practical Approach*, F. Eckstein, editor, Oxford University Press, Oxford, pp. 1-24 (1991), and incorporated herein by reference. Indirect synthesis may be performed in accordance biosynthetic techniques (e.g. polymerase chain reaction "PCR"), as described in Sambrook, J. et al., "Molecular Cloning, A Laboratory Manual", $2^{nd}$ edition 1989, incorporated herein by this reference.

Other methods of oligonucleotide synthesis include, but are not limited to solid-phase oligonucleotide synthesis according to the phosphotriester and phosphodiester methods (Narang, et al., (1979) *Meth. Enzymol.* 68:90), and to the H-phosphonate method (Garegg, P. J., et al., (1985) "Formation of internucleotidic bonds via phosphonate intermediates", *Chem. Scripta* 25, 280-282; and Froehler, B. C., et al., (1986a) "Synthesis of DNA via deoxynucleoside H-phosphonate intermediates", *Nucleic Acid Res.*, 14, 5399-5407, among others) and synthesis on a support (Beaucage, et al. (1981) *Tetrahedron Letters* 22:1859-1862) as well as phosphoramidate techniques (Caruthers, M. H., et al., "Methods in Enzymology," Vol. 154, pp. 287-314 (1988) and others described in "Synthesis and Applications of DNA and RNA," S. A. Narang, editor, Academic Press, New York, 1987, and the references contained therein, and nonphosphoramidite techniques. The chemical synthesis via a photolithographic method of spatially addressable arrays of oligonucleotides bound to glass surfaces is described by A. C. Pease, et al., Proc. Nat. Aca. Sci. USA (1994) 91:5022-5026. Oligoribonucleotide synthesis using phage RNA polymerase and ribonucleoside triphosphates is described by Milligan, J. F., et al., (1987) "Oligoribonucleotide synthesis using T7 RNA polymerase and synthetic DNA templates", *Nucl. Acids Res.* 15, 8783-8798; and using protected ribonucleoside phosphoramidites and chemical synthesis is described by Wu T., et al., (1989) "Prevention of chain cleavage in the chemical synthesis of 2'-O-silylated oligoribonucleotides", *Nucl. Acids Res.* 17, 3501-3517, among others.

For the purposes of the invention, the term "oligonucleotide" includes the term "polynucleotide", unless stated otherwise.

Oligonucleotide probe—an oligonucleotide employed to bind to another oligonucleotide.

Monomer—A member of the set of small molecules which can be joined together to form a polymer. The set of monomers includes but is not restricted to, for example, the set of common L-amino acids, the set of D-amino acids, the set of synthetic amino acids, the set of nucleotides and modified nucleotides, and the set of pentoses and hexoses. Other examples include abasic phosphodiesters, such as polyethers, and protein-nucleic acid (PNA) hybrids. As used herein, monomers refers to any member of a basis set for synthesis of a polymer. The monomer may be natural or synthetic. For example, dimers of the 20 naturally occurring L-amino acids form a basis set of 400 monomers for the synthesis of polypeptides. Different monomers may be used at successive steps in the synthesis of a polymer. Furthermore, a monomer may include protected members that are modified after synthesis.

Modified monomer—a naturally occurring monomer, obtained from a natural source or produced synthetically, that is chemically modified to add, replace, substitute, delete, or otherwise change one or more groups or bonds contained in the monomer. For the purposes of the invention, a monomer is modified, as mentioned above, to cause the modified monomer to preferentially hybridize or bind to another complementary monomer that is similarly modified.

Nucleotide—the monomeric unit of nucleic acid polymers, i.e., DNA and RNA, whether obtained from a natural source or produced synthetically, which comprises a nitrogenous heterocyclic base, which is a derivative of either a purine or pyrimidine, a pentose sugar, and a phosphate (or phosphoric acid). When the phosphate is removed, the monomeric unit that remains is a "nucleoside". Thus a nucleotide is a 5'-phosphate of the corresponding nucleoside. When the nitrogenous base is removed from the nucleotide, the monomeric unit that remains is a "phosphodiester". For the purposes of the invention, "nucleotide" includes its corresponding nucleoside and phosphodiester, and "oligonucleotide" includes its corresponding oligonucleoside and oligophosphodiester, unless indicated otherwise.

Modified nucleotide—a modified monomer in a nucleic acid polymer that contains a modified base, sugar and/or phosphate group. The modified nucleotide can be naturally occurring or produced by a chemical modification of a nucleotide either as part of the nucleic acid polymer or prior to the incorporation of the modified nucleotide into the nucleic acid polymer. For example, the methods mentioned above for the synthesis of an oligonucleotide may be employed. In another approach a modified nucleotide can be produced by incorporating a modified nucleoside triphosphate into the polymer chain during an amplification reaction. Examples of modified nucleotides, by way of illustration and not limitation, include dideoxynucleotides, derivatives or analogs that are biotinylated, amine modified, alkylated, fluorophore-labeled, and the like and also include phosphorothioate, phosphite, ring atom modified derivatives, and so forth. The present invention is directed, in part, to a particular type of chemical modification to one or more nucleotides.

Hybridization (hybridizing) and binding—to associate together. In the context of nucleotide sequences these terms are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by elevating the temperature, increasing the ratio of co-solvents, lowering the salt concentration, and the like. In the context of ligand/receptor, antibody/antigen, etc., binding depends on the affinity each of the specific binding pair for the other and means a relatively stable bond between respective pairs.

In accordance with the invention, the conventional hybridization solutions and processes for hybridization can be used, such as those described in J. Sambrook, E. F. Fritsch, T. Maniatis, *Molecular Cloning: A Laboratory Manual*, Cold Spring Harbor Laboratory Press, Cold Spring Harbor, Ed. $2^{nd}$, 1989, vol. 1-3, incorporated herein by reference. Conditions for hybridization typically include (1) high ionic strength solution, (2) at a controlled temperature, and (3) in the presence of carrier DNA and detergents and divalent cation chelators, all of which are well known in the art.

Complementary—A term directed to the affinity that one biological material has for binding to another biological material, such as members of a specific binding pair, as defined below. For example, particular antibodies are complementary to particular antigens, particular receptors to ligands and particular nucleotide to other nucleotides. With respect to nucleotide complements, two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence. Non-standard base pairing is also possible with nucleotide complements, for instance, the sequences may be parallel to each other and non-Watson-Crick base pairing may occur. Examples of the latter are complementary G=U or U=G base pairs in RNA sequences or complementary G=T or T=G base pairs in DNA sequences.

Substrate or surface—a porous or non-porous water insoluble material. The surface can have any one of a number of shapes, such as strip, plate, disk, rod, particle, including bead, and the like. The substrate can be hydrophobic or hydrophilic or capable of being rendered hydrophobic or hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly (4-methylbutene), polystyrene, polymethacrylate, poly(ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed. Common substrates used for arrays are surface-derivatized glass or silica, or polymer membrane surfaces, as described in Z. Guo et al. (cited above) and U. Maskos, E. M. Southern, *Nucleic Acids Res* 20, 1679-84 (1992) and E. M. Southern et al., *Nucleic Acids Res* 22, 1368-73 (1994), both incorporated herein by reference.

Immobilization of oligonucleotides on a substrate or surface may be accomplished by well-known techniques, commonly available in the literature. See, for example, A. C. Pease, et al., *Proc. Nat. Acad. Sci. USA,* 91:5022-5026

(1994); Z. Guo, R. A. Guilfoyle, A. J. Thiel, R. Wang, L. M. Smith, *Nucleic Acids Res* 22, 5456-65 (1994); and M. Schena, D. Shalon, R. W. Davis, P. O. Brown, *Science,* 270, 467-70 (1995), each incorporated herein by reference.

Label—a member of a signal producing system. Usually the label is part of a target nucleotide sequence or an oligonucleotide probe, either being conjugated thereto or otherwise bound thereto or associated therewith. The label is capable of being detected directly or indirectly. Labels include (i) reporter molecules that can be detected directly by virtue of generating a signal, (ii) specific binding pair members that may be detected indirectly by subsequent binding to a cognate that contains a reporter molecule, (iii) oligonucleotide primers that can provide a template for amplification or ligation or (iv) a specific polynucleotide sequence or recognition sequence that can act as a ligand such as for a repressor protein, wherein in the latter two instances the oligonucleotide primer or repressor protein will have, or be capable of having, a reporter molecule. In general, any reporter molecule that is detectable can be used.

The reporter molecule can be isotopic or nonisotopic, usually nonisotopic, and can be a catalyst, such as an enzyme, a polynucleotide coding for a catalyst, promoter, dye, fluorescent molecule, chemiluminescer, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, and the like The reporter molecule can be a fluorescent group such as fluorescein, a chemiluminescent group such as luminol, a terbium chelator such as N-(hydroxyethyl) ethylenediaminetriacetic acid that is capable of detection by delayed fluorescence, and the like.

The label can generate a detectable signal either alone or together with other members of the signal producing system. As mentioned above, a reporter molecule can be bound directly to a nucleotide sequence or can become bound thereto by being bound to an specific binding pair (sbp) member complementary to an sbp member that is bound to a nucleotide sequence. Examples of particular labels or reporter molecules and their detection can be found in U.S. Pat. No. 5,508,178, the relevant disclosure of which is incorporated herein by reference. When a reporter molecule is not conjugated to a nucleotide sequence, the reporter molecule may be bound to an sbp member complementary to an sbp member that is bound to or part of a nucleotide sequence.

Signal Producing System—the signal producing system may have one or more components, at least one component being the label. The signal producing system generates a signal that typically relates to the presence or amount of a target polynucleotide in a medium. A signal producing system may be incorporated on the oligonucleotide probes and relates to the presence of probes in a medium. The signal producing system includes all of the reagents required to produce a measurable signal. Other components of the signal producing system may be included in the developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, by use of electromagnetic radiation, desirably by optical examination. Signal-producing systems that may be employed in the present invention are those described more fully in U.S. Pat. No. 5,508,178, the relevant disclosure of which is incorporated herein by reference.

Member of a specific binding pair ("sbp member")—one of two different molecules, having an area on the surface or in a cavity that specifically binds to and is thereby defined as complementary with a particular spatial and polar organization of the other molecule. The members of the specific binding pair are referred to as cognates or as ligand and receptor (anti-ligand). These may be members of an immunological pair such as antigen-antibody, or may be operator-repressor, nuclease-nucleotide, biotin-avidin, hormones-hormone receptors, nucleic acid duplexes, IgG-protein A, DNA-DNA, DNA-RNA, and the like, and for the invention, may include members of a cross-linking pair.

Biological material—nucleic acids, such as DNA, RNA, polynucleotides, oligonucleotides, oligonucleotide probes, proteins, amino acids, antibodies, antigens, enzymes, coenzymes, ligands, receptors, hormones and labels, and monomers thereof, and genes that specify any of the above, and any other materials from any form of life and the synthetic versions of any of the above.

"Probe" or "Biological probe" means a biological material, such as a member of a specific binding pair of generally known make-up or composition, which is used to bind its complementary member of the respective specific binding pair to obtain information about a target material attached to the complementary member. The probe may be comprised of an oligonucleotide, antibody, antigen, ligand or a receptor, for example.

"Target", "Target sample", "Target material", or "biological target" means the biological material, synthetic or natural, which is under test or to be assayed. The target may be a oligonucleotide, or portion thereof, complementary to the. oligonucleotide probe; a complementary antigen, or portion thereof, to an antibody probe; a complementary antibody, or portion thereof, to an antigen probe; a complementary receptor or ligand, or portion thereof, to a respective ligand or receptor probe, for example.

"Sample" or "biological sample"—means a portion of a biological material, either natural or synthetic, comprising one or more target materials. A sample may be blood, urine, tissue, etc., or a component thereof, for example, from a patient, either mammal, animal, bacterial, or viral, or any other form of life.

DETAILED DESCRIPTION OF THE INVENTION

The present invention includes systems, tools and methods used to assay biological materials for diagnostic applications.

One or more biological samples having one or more biological targets per sample are multiplexed on a single array using the assay system 10 of the present invention. Referring to FIG. 1, assay system 10 comprises an array apparatus 11 having a substrate 12 with a surface 13 and a first plurality of biological probes, hereinafter called the capture probes C, which is covalently bound or linked to the surface 13 of the substrate 12 in an array pattern of features 14. The substrate can be made of conventional materials defined above and can be any shape that supports an array of features. Each capture probe $C_i$, where i=1→n, of the first plurality may be different and each different capture probe $C_i$ is located in a different feature location $14_i$ on the array 11. In a preferred embodiment, there are multiple copies (e.g., >10,000 molecules/ $um^2$) of each different capture probe $C_i$ covalently bound to each respective feature location $14_i$. Each capture probe $C_i$ will non-covalently "capture" a target of interest during an assay. The first plurality of capture probes C and therefore, the array apparatus 11, are universal or generic to the assay and to the biological materials being assayed.

Not all of the capture probe features C are illustrated in FIG. 1 for simplicity. In accordance with the invention, there may be over 10,000 (n=1 to >$10^4$) capture probe features $C_i$ on a single array apparatus 11, rendering the array system 10 capable of multiplexing as many unique combinations of biological samples-and-targets. Such an array system 10 will support the analysis of genes from the human genome, for example. Referring to FIG. 1, each individual feature $14_i$, for example, on the array has a plurality of the same capture probes $C_i$, respectively, covalently bound to the respective feature location. Capture probe $C_n$ is the "nth" capture probe feature on the array that has "n" total feature locations.

The capture probes C can either be synthesized in situ directly onto the substrate surface 13 or pre-synthesized and added as an intact species which is then covalently linked to the surface 13 of the substrate 12 using well-known conventional processes and materials. It is not the intent of the inventor to be limited to any synthesis method for the invention. Any synthesis method will work and all methods are within the scope of the invention. Information about the compositional makeup of each capture probe $C_i$ and the location on the array of each capture probe $C_i$ is maintained in a database. As a result, the array 11 is universal and can be manufactured in bulk quantities to reduce cost and turn around time. Likewise, the capture probes C for an assay are generic to the target material being assayed and can be manufactured in bulk quantities and added to the array substrate 12 as needed to reduce cost and turn around time. Customization of an assay of the present invention is provided by the solution probes S, described below.

The assay system 10 further comprises a second plurality of biological probes, namely the solution probes S. Each solution probe $S_{i,j}$, where j=1 to m, comprises a first region, called the anti-capture region, $\alpha C_i$, which is complementary and binds to a respective capture probe $C_i$ on the array substrate 12. For example, for capture probe $C_1$, the complementary anti-capture region of the solution probe $S_{1,j}$ is $\alpha C_1$ (and for capture probe $C_2$, the solution probe is $S_{2,j}$ and the complementary anti-capture region is $\alpha C_2$; for $C_3$, is $S_{3,j}$ and $\alpha C_3$; . . . for $C_n$, is $S_{n,m}$ and $\alpha C_n$, respectively).

Each solution probe $S_{i,j}$ further comprises a second region, called the anti-target region, $\alpha T_j$, which is complementary and binds to a target $T_{j,k}$ of interest from a sample, or patient $P_k$, where m equals the number of different targets in a sample P and k=1→x, where x equals the number of samples. The anti-capture region $\alpha C$ and the anti-target region $\alpha T$ of the solution probe S may be separately manufactured. The anti-target region $\alpha T$ may be linked to the anti-capture region $\alpha C$ of the solution probe S with a strong non-covalent bond, and preferably, the two regions of the solution probe S are linked covalently. Alternatively, the anti-capture region $\alpha C$ and the anti-target region $\alpha T$ may be regions of a continuous sequence of monomers of the same biological type that make up the solution probe S, wherein the linkage between the two regions is a conventional linkage between two monomers of a polymer.

The anti-capture regions $\alpha C$ of the set of the solution probes S are simply the complements to the generic set of capture probes C on the universal array apparatus 11. Therefore, the anti-capture regions $\alpha C$ can be manufactured separately and stored in bulk until needed to form a complete solution probe S for an assay. Moreover, the anti-target regions $\alpha T$ can be either synthesized directly on the anti-capture regions $\alpha C$, or synthesized separately and linked to the anti-capture regions $\alpha C$ as an intact species using well known methods of synthesizing and linking. This provides a time and cost savings benefit. Alternatively, the anti-capture regions $\alpha C$ and the anti-target regions $\alpha T$ of the solution probe S can be manufactured together when the information about samples P and targets T for the assay are known. In accordance with the invention, each capture probe $C_i$ on the apparatus 11 is an address and, for a given experiment, corresponds to a predetermined biological target from a biological sample (or target-sample combination $T_j$-$P_k$). The customization of the array is accomplished by the plurality of solution probes, which are customized to deliver the target-sample combinations to the corresponding capture probe locations (i.e. "addresses") on the array apparatus 11. In the preferred embodiment, these addresses are stored in a computer for the particular multiplexing assay.

To address a particular target $T_j$-sample $P_k$ combination (hereinafter abbreviated as $T_j$-$P_k$ or $T_{j,k}$) to a particular capture probe $C_i$ location $14_i$ on the array apparatus 11 for an assay in accordance with the invention, the anti-capture region $\alpha C_i$ of a respective solution probe $S_{i,j}$ must be complementary to the capture probe $C_i$ that corresponds to the particular target-sample combination $T_j$-$P_k$. Further, the anti-target region $\alpha T_j$ of the respective solution probe $S_{i,j}$ must be complementary to the particular target $T_j$ of the target-sample combination. For example, if it has been predetermined that the target-sample combination $T_{10,k}$ is to be assembled at capture probe $C_5$ on the array apparatus 11 for a given experiment or assay, then the solution probe S which will address the target $T_{10,k}$ to capture probe $C_5$ is the solution probe $S_{5,10}$. The solution probe $S_{5,10}$ has an anti-target region $\alpha T_{10}$, which is customized to bind to the target $T_{10}$, and has an anti-capture region $\alpha C_5$, which is customized to bind to the capture probe $C_5$. In this example, the target $T_{10}$ can be from all samples $P_{1 \to x}$ or from one sample $P_k$, or target $T_{10}$ can be one of multiple different targets $T_{1 \to m}$ from multiple samples $P_{1 \to x}$, depending on the type of multiplexing assay to be performed.

Figure 2:
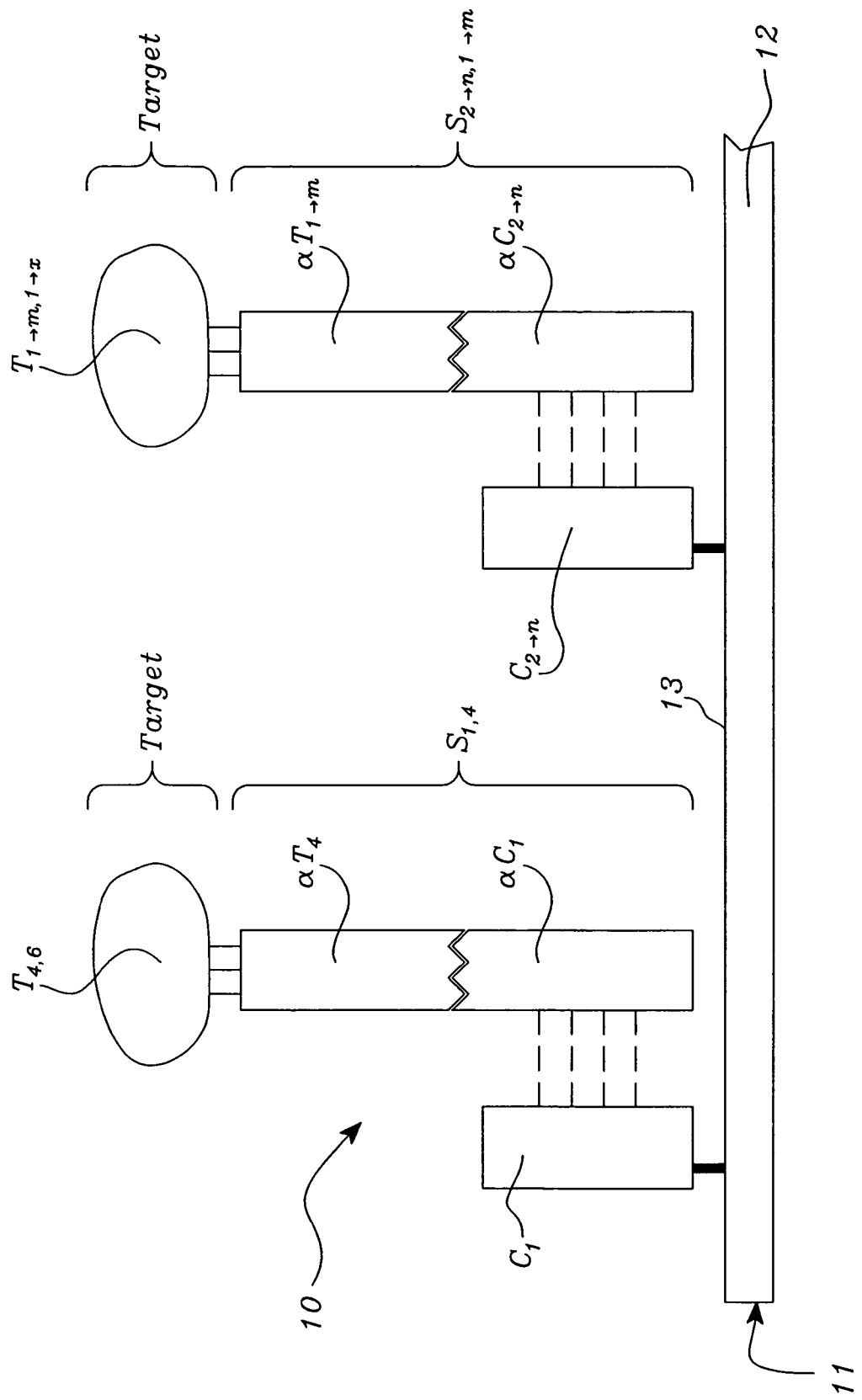
FIG. 2 is a magnified side view illustrating biological targets assembled to one embodiment of the system of the present invention after an assay.

The plurality of solution probes S of the present assay system 10 are customized for each assay. FIG. 2 illustrates the assembly of target-sample combination $T_4$-$P_6$ or $T_{4,6}$ to the array apparatus 11. The anti-capture region $\alpha C_1$ of the solution probe $S_{1,4}$ is made complementary to the capture probe $C_1$ at a known location on the array 11. Further, the anti-target region $\alpha T_4$ of that solution probe $S_{1,4}$ is made to be complementary to the target $T_{4,6}$. During the assay, the particular target $T_{4,6}$, if present in a biological sample $P_6$ under test, will hybridize to the particular solution probe $S_{1,4}$ at its anti-target region $\alpha T_4$. Moreover, the hybridized target $T_{4,6}$-solution probe $S_{1,4}$ will hybridize via its anti-capture region $\alpha C_1$ to the corresponding capture probe $C_1$ on the array, such that the presence of the particular target $T_4$ in the particular sample $P_6$ will be ascertainable by the presence of the target $T_{4,6}$ on the array 11 at the known location of capture probe $C_1$ after the assay. Likewise, multiple different targets $T_{1 \to m}$ in the same or multiple different samples $P_{k=1 \to x}$, can be assayed along with target $T_4$ on the same array apparatus 11 at capture probes $C_{2 \to n}$ using respective solution probes $S_{2 \to n, 1 \to m}$. The assay system 10 can multiplex one or more biological samples, having one or more biological targets per sample all on the same array apparatus 11 using the customized solution probes S and the generic capture probes C on the array apparatus 11 of the present invention. It should be noted that the addressing numbering system used in the description of the invention herein is illustrative only. Other addressing systems could be used, as should be obvious to one skilled in the art.

Therefore, it is within the scope of the present invention to use any appropriate addressing system on the multiplexing array.

Figure 3:
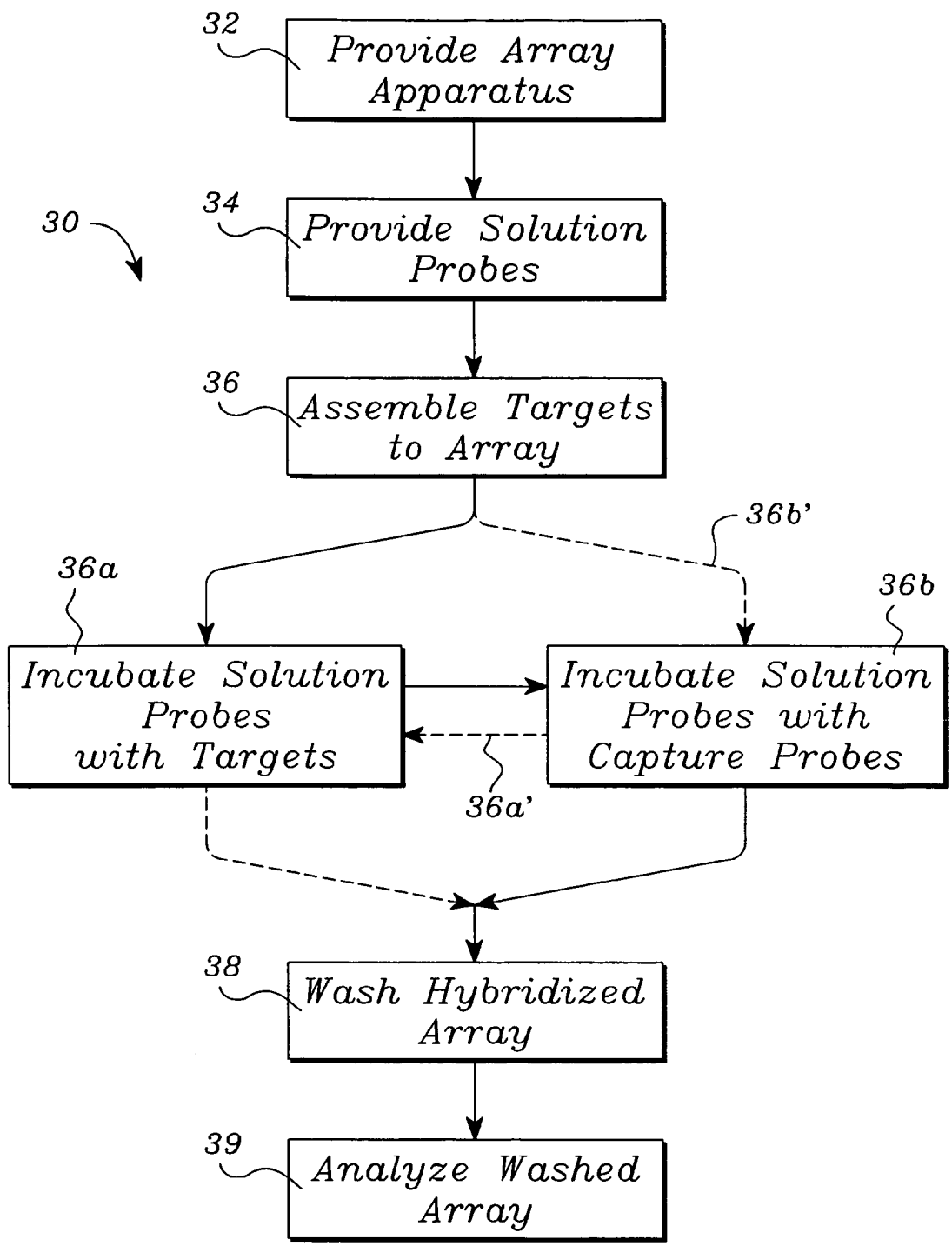
FIG. 3 is a block diagram illustrating a method of multiplexing biological materials on an array in accordance with one embodiment of the invention.

The assay method 30 of multiplexing on a single array one or more biological samples, having one or more biological targets per sample, according to the present invention, is illustrated in FIG. 3. The assay method 30 uses the assay system 10, as described above. The assay method of multiplexing 30 comprises the steps of providing (32) the array apparatus 11 comprising the substrate 12 with a first plurality of biological probes (capture probes C) in an array pattern on the surface 13 of the substrate 12. Each capture probe $C_i$ within the first plurality C is different and each different probe $C_i$ is located in a different feature location on the array apparatus 11. In the preferred embodiment, there are multiple copies of each different capture probe $C_i$ at each feature location on the array 11 to improve the accuracy of the assay.

The assay method 30 of multiplexing further comprises the step of providing (34) the second plurality of biological probes, called solution probes S for the assay system 10. Each solution probe $S_{i,j}$ of the second plurality S comprises a first region (anti-capture region $\alpha C_i$) and a second region (anti-target region $\alpha T_j$). As described above, the solution probes S are customized to deliver the different target-sample combination to be assayed to their corresponding capture probes $C_i$ on the array (i.e. "addresses"). The first regions $\alpha C_i$ of each solution probe $S_{i,j}$ are customized to be complementary to respective different capture probe $C_i$ on the array 11. The second regions $\alpha T_j$ of each solution probe $S_{i,j}$ are customized to be complementary to respective targets $T_j$. The customization of the solution probes S predetermines which capture probe $C_{i=1 \rightarrow n}$ feature on the array will receive a particular target-sample combination $T_{j, k}$. The customized solution probes S also deliver or assemble the respective target-sample combinations onto the array at their corresponding addressed capture probe C locations.

The assay method 30 of multiplexing biological materials on a single array further comprises the step of assembling (36) one or more respective target $T_{j, k}$ from the one or more biological samples $P_k$ to the array apparatus 11 for evaluation. If present in the particular sample $P_k$ under test, the target $T_{j, k}$ is assembled onto the array apparatus 11 at capture probe feature $C_i$ by the solution probe $S_{i,j}$ via a hybridization process. The hybridization process may be simultaneous or preferably in two hybridization steps. The sequence of the hybridization steps or the use of a simultaneous hybridization is not crucial, except where there are multiple samples being assayed, as further described below. However, in the preferred two step hybridization process, the hybridization of the targets T with the solution probes S in the solution phase is preferred. In one hybridization step (step 36a), a target $T_j$, from a sample $P_k$ is pre-incubated with the solution probe $S_{i,j}$ to allow the binding or hybridization to occur in solution between the target $T_{j, k}$ and the anti-target region $\alpha T_j$ of the solution probes $S_{i,j}$ using well-known conventional methods of hybridization. Preferably, this hybridization step 36a is performed first. The concentration of the solution probes S is equivalent to or in excess of the expected concentration of the target T. Preferably, the concentration of solution probes S is in sufficient excess, such that the free concentration of the solution probes S is not decreased more than 10% from binding to its target T. After the pre-incubation step (36a), the other hybridization step (step 36b) includes applying the hybridized {target $T_{j, k}$-solution probe $S_{i,j}$} species in solution to the array apparatus 11 under well-known conditions for hybridization or binding between the respective capture probe $C_i$ and the anti-capture $\alpha C_i$ region of the solution probe $S_{i, j}$ to occur. Alternatively, under some circumstances, the hybridization steps can be reversed, but as with the simultaneous hybridization, the advantages of hybridizing the solution probes with the target in solution are not available. In this alternate hybridization procedure, the solution probe $S_{i,j}$ can be pre-incubated with the capture probe $C_i$ on the apparatus 11 (step 36b'). Then the target $T_{j, k}$ is added to the (capture probe-solution probe) system 10 for binding to the anti-target region $\alpha T_j$ of the solution probes $S_{i, j}$ (step 36a'). In all situations, the hybridization or binding is performed under well-known conditions in the art.

The assay method 30 of multiplexing further comprises the step of washing (38) the hybridized array apparatus 11 to remove unhybridized/unbound material using conventional materials and processes; and the step of analyzing (39) the results of the assay, according to conventional methods.

According to the invention, either the capture probes C, solution probes S and/or the targets T are labeled at any step(s) before or during the assay process to either directly or indirectly produce a signal, such as fluorescence or radiation, for example, using conventional labeling techniques and materials. The present invention does not require a particular labeling method or materials and it is believed that any of the conventional techniques and materials will work with the invention. The hybridized array 11 is analyzed (39) using conventional equipment, such as optical scanning, to track, sort, identify and/or further characterize the targets $T_{1 \rightarrow m}$ in the samples $P_{1 \rightarrow x}$ assayed.

Figure 4A:
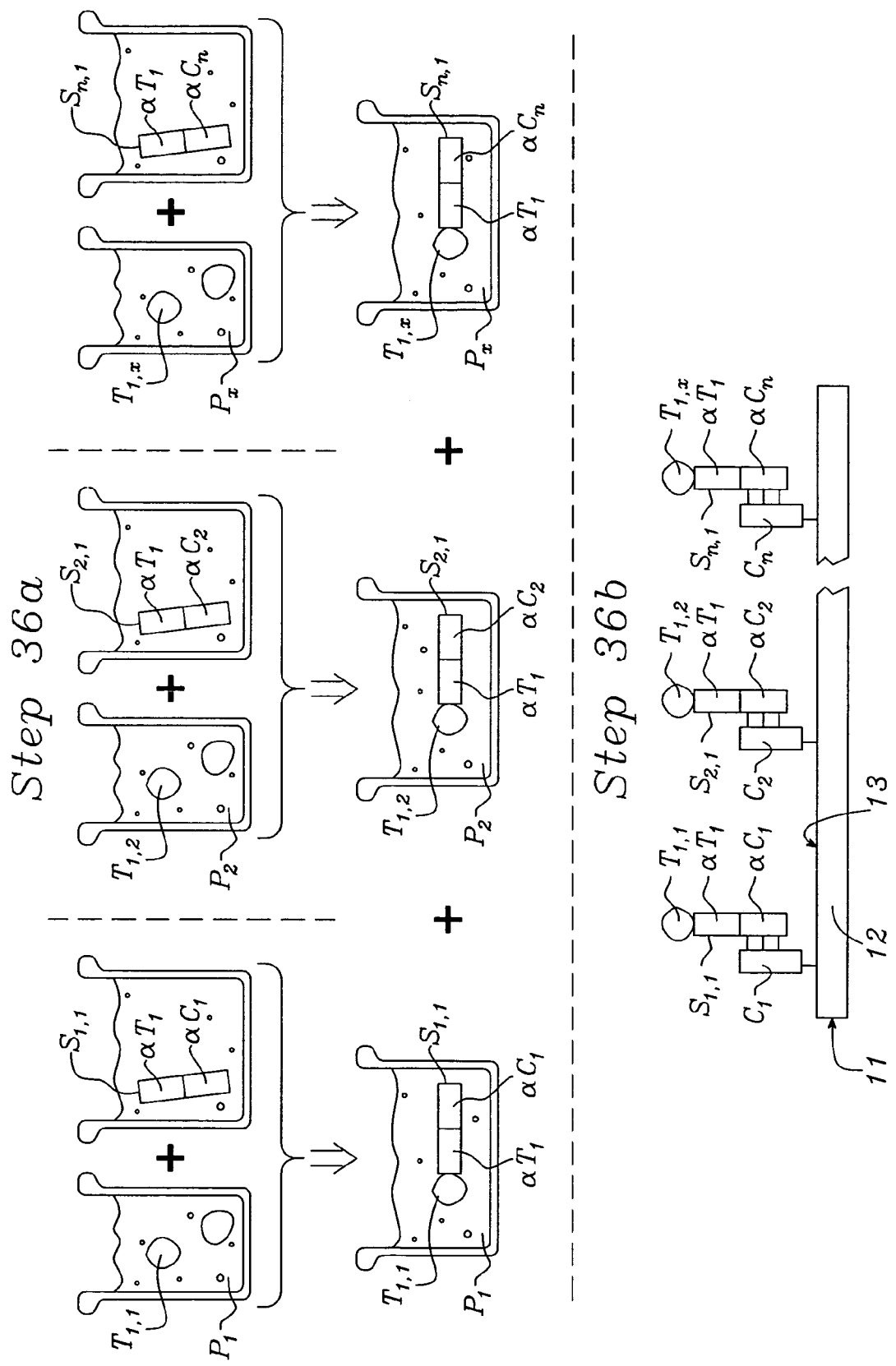
FIG. 4A is a diagram illustrating multiplexing of a single target type from multiple samples on a single array in accordance with one embodiment of the system of the present invention.
Figure 4B:
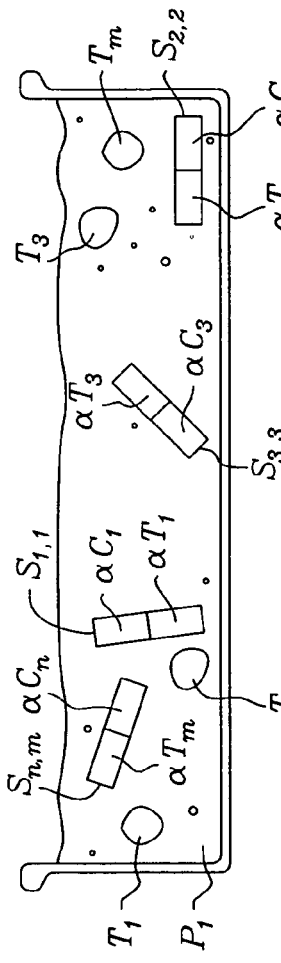
FIG. 4B is a diagram illustrating multiplexing of multiple different targets from one sample on a single array using the system according to one embodiment of the present invention.
Figure 4B:
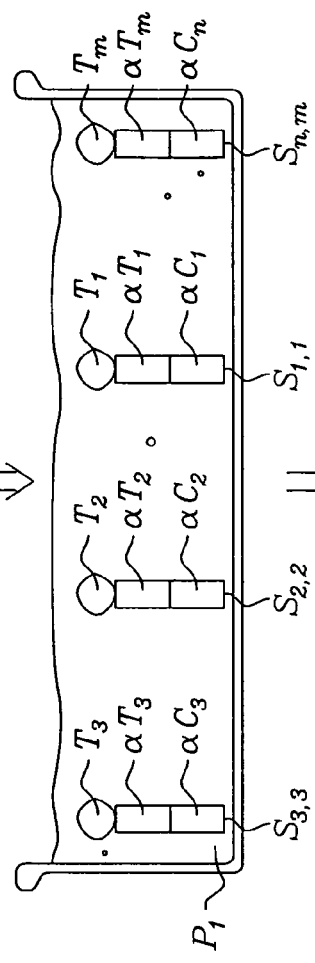
Figure 4B:
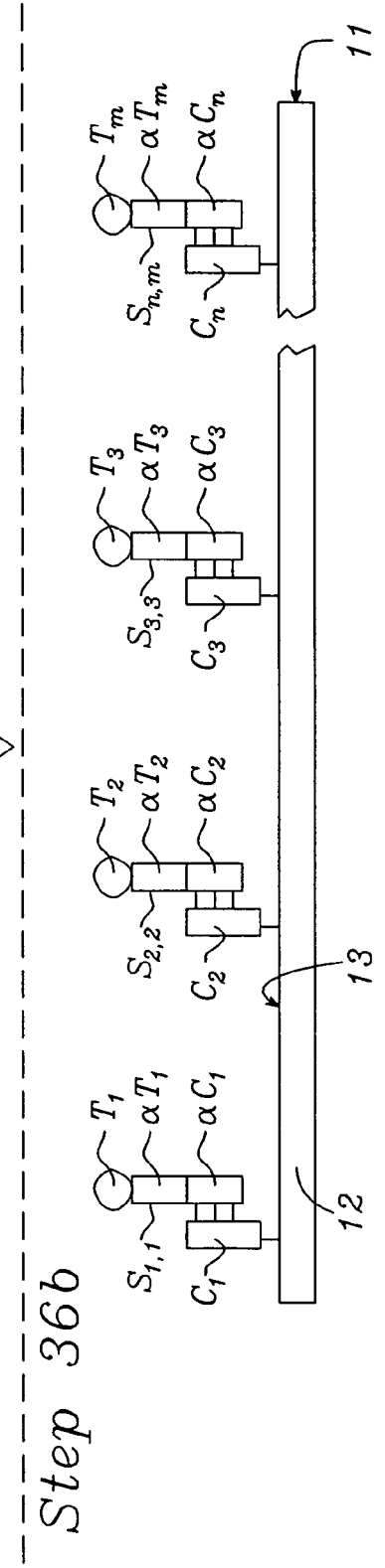

FIGS. 4A and 4B illustrate the concept of multiplexing in accordance with the invention. In FIG. 4A, the assay will determine whether a particular target $T_1$ is present in multiple samples $P_{1 \rightarrow x}$ (e.g., from multiple patients). In this embodiment, samples $P_{1 \rightarrow x}$ are kept in separate vessels. Solution probes $S_{1 \rightarrow n, 1}$ are provided, each with a different anti-capture $\alpha C_{1 \rightarrow n}$ region corresponding to the different capture probe addresses $C_{1 \rightarrow n}$ on the array where it has been predetermined that the different samples $P_{1 \rightarrow x}$ will be assembled for a given assay. Moreover, the solution probes $S_{1 \rightarrow n, 1}$ have the same anti-target region $\alpha T_1$, because only one target $T_{j=1}$ is being sought in multiple samples $P_{1 \rightarrow x}$. Only the anti-capture regions $\alpha C_{1 \rightarrow n}$ on the solution probes $S_{1 \rightarrow n, 1}$ distinguish the samples from one another. Therefore, each of the different solution probes $S_{1 \rightarrow n, 1}$ are added to the separate vessels containing the respective samples $P_{1 \rightarrow x}$. During the hybridization step 36a, sample $P_1$ is pre-incubated with solution probes $S_{1, 1}$, and separately, sample $P_2$ is pre-incubated with solution probes $S_{2, 1}$, and so on, to the last sample $P_x$ being separately pre-incubated with solution probes $S_{n, 1}$. Note that features may be incremented with replicates, control probes, etc., such that n does not equal x. The indexing used herein is just an example and depends upon the array design, that is, use of replicate features for samples, control samples, etc.

After the hybridization step 36a is completed, the hybridized species may be mixed together for the second hybridization step 36b. During step 36b, the {hybridized targets $T_{1, 1 \rightarrow x}$-solution probes $S_{1 \rightarrow n, 1}$} complexes are incubated with the array apparatus 11. Since the targets $T_{1, 1 \rightarrow x}$ were addressed to be assembled on respective capture probes $C_{1 \rightarrow n}$ by the solution probes $S_{1 \rightarrow n, 1}$, solution probes $S_{1,1}$ will assemble the target $T_{1,1}$ on capture probe $C_1$. Therefore, any targets $T_1$ present at probe location $C_1$, as a result of the hybridization steps 36a, 36b, originated from sample $P_1$. The same is true for the targets $T_1$ from the other samples $P_{2 \rightarrow x}$ and the other respective capture probes $C_{2 \rightarrow n}$ and solution probes $S_{2 \rightarrow n, 1}$. The system 10 and method 30 essentially self-assemble the targets $T_{1, 1 \rightarrow x}$ during the assay. After the hybridized array apparatus 11 is washed 38, the assay results are analyzed 39. The analysis step 39 will reveal whether and how much, among other things, of target $T_1$ is present in samples $P_{1 \to x}$. The alternative simultaneous hybridization and reversed hybridization steps 36a' and 36b' are not recommended when a target from more than one sample is being assayed.

FIG. 4B illustrates an example of multiplexing multiple different targets $T_{1 \to m}$ from one sample $P_{k=1}$, on a single array according to the invention. FIG. 4B illustrates a single vessel containing a solution of multiple (different) targets $T_{1 \to m, 1}$ and different solution probes $S_{1 \to n, 1 \to m}$. In this example, the solution probes $S_{1 \to n, 1 \to m}$ have both different anti-capture regions $\alpha C_{1 \to n}$, and different anti-target regions $\alpha T_{1 \to m}$. The anti-target regions are customized to the targets $T_{1 \to m, 1}$ under test. The anti-capture regions are customized to correspond to the different generic capture probes $C_{1 \to n}$, in order to deliver the hybridized targets to the appropriate addresses on the array. The different anti-target regions $\alpha T_{1 \to m}$ of the different solution probes $S_{1 \to, 1 \to m}$ will hybridize with their respective targets $T_{1 \to m, 1}$ in step 36a. The different anti-capture regions $\alpha C_{1 \to n}$ of the different {hybridized target $T_{1 \to m, 1}$-solution probes $S_{1 \to n, 1 \to m}$} species will hybridize with their respective capture probes $C_{1 \to n}$ on the array apparatus 11 in step 36b. Since there is only one sample $P_1$ in this example, whether and how much, among other things, of the particular targets $T_{1 \to m}$ are present in the sample $P_1$ can be ascertained by their presence at their respective addressed capture probe locations $C_{1 \to n}$ on the array during analysis. Moreover, the alternative simultaneous hybridization or the reversed hybridization steps 36a', 36b' can be used in such assays of one sample, as provided in the example illustrated in FIG. 4B.

Figure 4C:
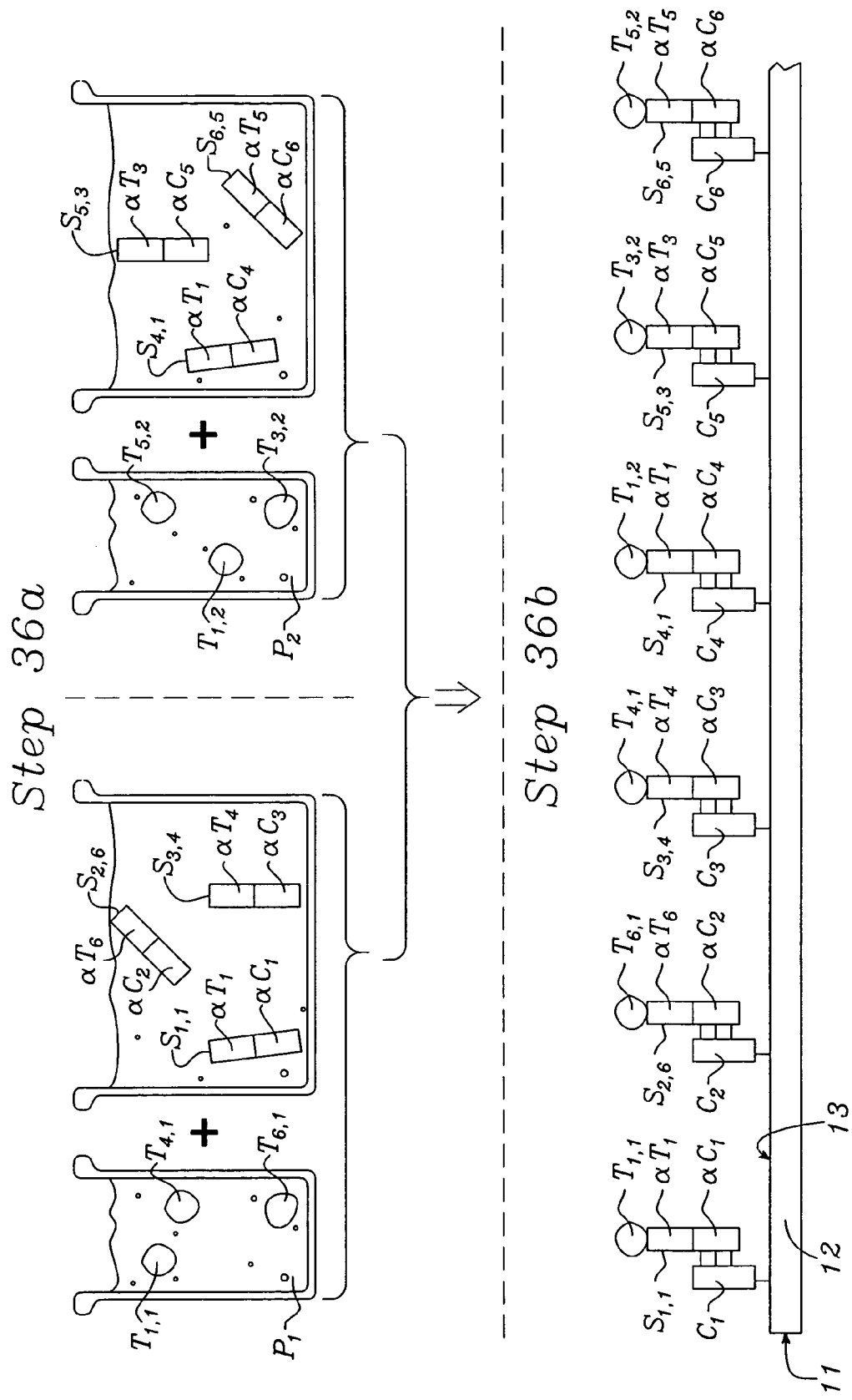
FIG. 4C is a diagram illustrating multiplexing of multiple different targets from multiple different samples on a single array using the system according to one embodiment of the present invention.

FIG. 4C illustrates the assay of multiple different targets $T_{1 \to m}$ from multiple different samples $P_{1 \to x}$ using the plurality of solution probes $S_{1 \to, 1 \to m}$ that each have both different anti-capture regions $\alpha C_{i \to n}$ and different anti-target regions $\alpha T_{1 \to m}$. The anti-capture regions are customized to correspond to the different generic capture probes $C_{1 \to n}$, in order to deliver the hybridized targets to the appropriate addresses on the array. The anti-target regions are customized to the targets $T_{1 \to m, 1 \to x}$ under test. This customization of solution probes provides an assembly of the different target-sample combinations onto the array at pre-determined capture probe locations $14_{1 \to n}$ (i.e. "addresses") for evaluation. The vessels containing respective samples $P_{1 \to x}$ must be kept separated, and the different solution probes $S_{1 \to n, 1 \to m}$ customized for the respective samples $P_{1 \to x}$ are pre-incubated only with the respective separate samples $P_{1 \to x}$. After pre-incubation (step 36a), the hybridized probes $S_{1 \to n, 1 \to m}$ can be combined for the hybridization step 36b with the capture probes $C_{1 \to n}$ on the array apparatus 11. The alternative simultaneous hybridization or the reversed hybridization steps 36a', 36b' are not recommended for the example illustrated in FIG. 4C. The different solution probes $S_{1 \to n, 1 \to m}$ will sort and assemble the different targets $T_{1 \to m, 1 \to x}$ from the different samples $P_{1 \to x}$ onto the array 11 according to the predetermined addresses provided by the capture probe locations $14_{1 \to n}$.

As illustrated in FIG. 4C, target $T_{1,1}$ from sample $P_1$ was addressed and assembled on capture probe $C_1$ with solution probe $S_{1,1}$, such that the presence and quantity of a target $T_{1,1}$ in sample $P_1$ can be ascertained by its presence at its corresponding capture probe location $C_1$ on the array during analysis. Moreover, targets $T_{6,1}$ and $T_{4,1}$ from sample $P_1$ were addressed and assembled on capture probes $C_2$ and $C_3$, with solution probes $S_{2,6}$ and $S_{3,4}$, respectively, for evaluation. From sample $P_2$, targets $T_{1,2}$, $T_{3,2}$ and $T_{5,2}$ were addressed and assembled on capture probes $C_4$, $C_5$ and $C_6$ by solution probes $S_{4,1}$, $S_{5,3}$ and $S_{6,5}$, respectively, for evaluation.

It should be understood that the number of samples and the number of targets per sample that are multiplexed on a single array 11 with the assay system 10 and method 30 of the present invention are only limited by the number of different capture probes C present on the array apparatus 11. Therefore, the discussion above and examples illustrated in FIGS. 3, 4A, 4B and 4C are merely illustrative of all of the many numerous different combinations of samples-and-targets that can be multiplexed on the single array 11, according to the present invention.

The solution probes S of the present invention are unique assay tools in that they were developed to improve the accuracy of conventional sandwich hybridization assays so that sandwich hybridization assays can be performed effectively on arrays. In addition, the solution probes S of the present invention advantageously expand the usefulness of the sandwich hybridization assay on an array to multiplexing one or more biological samples having one or more targets per sample on a single array. The ability to customize the solution probes S to both biological targets T and to the capture probes C on the array facilitate the assembly of the targets T in predetermined locations on the array surface 13 during a given assay and make multiplexing on the array possible. Therefore, the set of solution probes S of the present invention is a robust tool for multiplexing one or more samples, having one or more targets per sample on a single addressable and self-assembling array. Moreover, the customization of the solution probes S allows the array apparatus 11 and capture probes C to be generic to the assay and produced in bulk, which is more cost effective.

The processes and materials used for the manufacture of the array system 10 and the ancillary materials used for the assay method 30 will depend on the biological materials that are used and analyzed. The system 10 is manufactured using conventional well-known processes and materials. Table 1 provides a list of biological materials that are useful for the capture probes C, solution probes S and targets T of the invention. It should be understood by those skilled in the art that the present invention has broad application to biological material analysis and that the present system 10 and method 30 are configurable to accommodate any biological material, such that the combinations listed in Table 1 are illustrative only. For information regarding the processes and materials used for the manufacture of arrays of biological materials, such as proteins, antibodies, or the like in accordance with the is invention, see for example U.S. Pat. Nos. 4,591,570; 5,143,854; and 5,252,743 and the following articles: Ekins, R., et. al., "Development of microspot multi-analyte ratiometric immunoassay using dual fluorescent-labeled antibodies" *Analytica Chimica Acta*, (1989), 227:73-96; and Ekins, R P and F W Chu. "Multianalyte microspot immunoassay—microanalytical 'compact disc' of the future" (1991). There are several common methods for attaching oligonucleotides to proteins and ligands, most preferably the use of biotin-avidin to cross-link the species. Other methods to cross-link species include the use of homobifunctional or heterobifunctional groups (e.g. to cross-link an amine-derivatized oligonucleotide to a protein). Materials and methods for using biotin-avidin, as well as for bifunctional group cross-linking, are available from Pierce (Rockford, Ill.). For oligonucleotide synthesis, see the references cited in the Definitions section above.

TABLE 1

Species of Biological Material for Capture
Probes, Solution Probes and Target Samples

|    | Capture Probes    | Anti-Capture Region | Anti-Target Region  | Target Sample       |
|----|-------------------|---------------------|---------------------|---------------------|
| 1  | Oligonucleotide   | Oligonucleotide     | cDNA                | Oligonucleotide (e.g., mRNA) |
| 2  | Oligonucleotide   | Oligonucleotide     | PCR Product         | Oligonucleotide (e.g., mRNA) |
| 3  | Oligonucleotide   | Oligonucleotide     | Oligocleotide       | Oligonucleotide     |
| 4  | Oligonucleotide   | Oligonucleotide     | Antibody            | Antigen             |
| 5  | Oligonucleotide   | Oligonucleotide     | Antigen             | Antibody            |
| 6  | Antigen           | Antibody            | Oligonucleotide     | Oligonucleotide     |
| 7  | Antigen           | Antibody            | cDNA or PCR Product | Oligonucleotide     |
| 8  | Antibody          | Antigen             | Oligonucleotide     | Oligonucleotide     |
| 9  | Antibody          | Antigen             | cDNA or PCR Product | Oligonucleotide     |
| 10 | Oligonucleotide   | Oligonucleotide     | Receptor            | Ligand              |
| 11 | Oligonucleotide   | Oligonucleotide     | Ligand              | Receptor            |
| 12 | Receptor          | Ligand              | Oligonucleotide     | Oligonucleotide     |
| 13 | Ligand            | Receptor            | cDNA or PCR Product | Oligonucleotide     |

The present system 10 can be packaged as a kit with instructions for use in accordance with the method 30 and provided to users, such as research and/or analytical laboratories, for practicing the multiplexing assay in accordance with the invention. The user need only specify the type of capture probes they want their kit to contain and the necessary information about the biological materials that the user will be assaying. The solution probes S can be customized to the user's specifications. Thus, each solution probe S of a particular set may comprise first regions selected from oligonucleotides, antibodies, antigens, ligands and receptors, for example, depending on the biological make-up of the biological features on the array apparatus 11 in the kit. Further, the second regions of the set of solution probes S of the kit may comprise second regions selected from cDNA, PCR products, oligonucleotides, antibodies, antigens, ligands and receptors, for example, depending on the biological make-up of the biological targets to be assayed by the user. For example, a user may request a kit containing a set of solution probe S, wherein each solution probe S may comprise a different antigen linked to the same or a different cDNA, wherein the different antigens are complementary to a plurality of different antibody features on the array apparatus 11 and the cDNA is complementary to oligonucleotide (e.g., mRNA) target material(s) to be assayed (see for example, Table 1, examples 8 and 9). The set of solution probes S in the kit delivers each target material T being assayed by the user to a predetermined "address" or capture probe C on the universal array 11. During the assay, the set of solution probes S will essentially deliver or assemble each target material T to its corresponding address to provide an addressable and self-assembling array to the user. The kit is particularly useful for multiplexing assays of one or more biological sample(s), having one or more biological target(s) per sample, on a single array.

In another embodiment of the present invention, an assay system 20 for assaying biological materials that has good specificity and sensitivity is provided. The assay system 20 has good specificity by providing a reduced likelihood of cross hybridizations between noncomplementary materials. The assay system 20 has good sensitivity by providing a reduced likelihood of intramolecular structures within the biological probes. The assay system 20 comprises an assay apparatus 21 that has a first set of biological material probes, called capture probes 2C, on the surface 23 of a substrate 22. The capture probes 2C each comprises a sequence of monomers. The sequence of monomers in each capture probe comprises one or more modified monomer(s) M, as defined herein and above, to preferentially hybridizes with complementary similarly modified monomer(s) M. The set of capture probes 2C is generic to all assays of biological target material.

As mentioned above for the assay system 10, the capture probes 2C for the system 20 can be synthesized in situ directly onto the substrate 22, added as a intact species which is then covalently linked to the substrate 22, or provided using other processes and materials, all of which are within the scope of the invention. The modified monomer M is synthesized into the sequence of monomers using the same conventional methods. As a result, the apparatus 21 is universal and generic with respect to the target material to be tested. The apparatus 21 can be manufactured in bulk quantities to reduce cost and turn around time. Likewise, the set of capture probes 2C are generic and can be manufactured in bulk quantities and added to the substrate 22 as needed to reduce cost and turn around time. Customization of the assay system 20 is provided by the solution probes 2S, described below.

The assay system 20 having good specificity and sensitivity further comprises a second set of biological material probes, called solution probes 2S. The set of solution probes 2S are similar to the solution probes S of system 10 in that the set of solution probes 2S indirectly links or assembles target materials 2T to be tested to the assay substrate 22 for analysis. Moreover, there is a different set of solution probes 2S for each type of biological material being tested. Customization of an assay is accomplished with the customization of the solution probes 2S to the biological targets 2T to be assayed and to the capture probes 2C on the apparatus 21. The solution probes 2S comprise a first sequence region of monomers, called an anti-capture sequence α2C, that is customized to be complementary to the sequence of monomers in the capture probe 2C, for hybridizing or binding to the capture probe 2C. The set of solution probes 2S further comprises a second sequence region, called an anti-target sequence α2T, that is customized to be complementary to a target 2T under test, for hybridizing or binding to the target 2T. The two-part customization of the solution probes 2S renders the system 20 particularly useful for sandwich hybridization assays.

The set of solution probes 2S is different from the solution probes S of system 10 in that the anti-capture sequence regions α2C comprise one or more modified monomer(s) M that preferentially hybridize with complementary similarly modified monomer(s) M of the capture probes 2C. Therefore, the system 20 has good specificity because the preferential binding between the similarly modified monomers M of the complementary capture probes 2C and the anti-capture sequence regions α2C provides a reduced likelihood of cross hybridizations (e.g., hybridizations with mismatches) between noncomplementary sequences. Moreover, the system 20 has good sensitivity due to the presence of modified monomers M interspersed among the unmodified (or not similarly modified) monomers. Since the binding of complementary modified monomers M to unmodified monomers is not favored thermodynamically, there is a reduced likelihood of intramolecular structures, such as hairpins, forming within the capture probes 2C or within the anti-capture sequence regions α2C.

As mentioned above for assay system 10, Table 1 lists the biological materials useful for the system 20 of the present invention without limitation. However, the discussion below will focus on species 1-5 and 10-11 of the preferred embodiment, having oligonucleotides for the capture probe 2C and anti-capture region α2C. Table 1 lists representative anti-target regions, α2T and target 2T sample species selected from, but not limited to, oligonucleotides, mRNAs, cDNAs, PCR products, antibodies, antigens, ligands and receptors, for species 1-5 and 10-11. These and other complementary biological materials will work in the preferred embodiment of the present invention.

In the preferred embodiment, the oligonucleotide capture probe 2C and complementary oligonucleotide region α2C of the solution probe 2S are synthesized with one or more complementary reversed polarity nucleotides, such that the nucleotides with reversed polarity will preferentially hybridize to complementary reversed polarity nucleotides. The reversed polarity nucleotides preferentially hybridize to each other rather than to a complementary non-reversed polarity nucleotide because it is thermodynamically more favorable, as is further described below.

The term "reversed polarity" used here is the same as the term "inverted polarity" defined in U.S. Pat. Nos. 5,399,676; 5,527,899; and 5,721,218, mentioned above, which are incorporated herein by reference. The oligonucleotide probe 2C and region α2C of the invention each contains at least one monomer that has opposite or reversed polarity relative to the polarity of the growing oligonucleotide sequence. The polarity of the growing oligonucleotide sequence is determined, for the purposes of the invention, from the polarity of the first synthesized nucleotide of the oligonucleotide sequence.

Conventional synthesis of an oligonucleotide is in the (5'→3') direction, wherein the 5'-end of a growing oligonucleotide chain attaches to a new nucleotide at the new nucleotide's 3'-end during synthesis (hereinafter the oligonucleotide is referred to as having a "(5'→3') polarity"). This conventional synthesis forms (5'→3') internucleotide linkages between adjacent nucleotides in the sequence. Moreover, it is not uncommon for oligonucleotide synthesis to be performed in the (3'→5') direction, wherein the 3'-end of the growing oligonucleotide chain attaches to a new nucleotide at the new nucleotide's 5'-end during synthesis (hereinafter the oligonucleotide is referred to as having a "(3'→5') polarity"). The (3'→5') synthesis direction forms (3'→5') internucleotide linkages between adjacent nucleotides in the sequence.

However, what is uncommon, is to synthesize an oligonucleotide with a mixture of both synthesis directions, thereby forming oligonucleotides comprising both (5'→3') and (3'→5') synthesis orientations or "polarities" in the same oligonucleotide. As a consequence, the oligonucleotide with the mixture of synthesis orientations comprises both heterogeneous (5'→3') and (3'→5') internucleotide junctions or linkages and homogenous (3'→3') and (5'→5') internucleotide linkages. Hereinafter the (3'→3') and (5'→5') internucleotide linkages are each referred to as "an inverted polarity linkage", since they are formed at the junction between two nucleotides where there has been a switch from one polarity to the opposite polarity during synthesis. Moreover, the combination or mixture of polarities in a nucleotide sequence is not normally found in nature. Therefore, not wanting to be limited to one conventional synthesis direction or the other, one way to define a "reverse polarity nucleotide N", for the purposes of this invention, is a nucleotide that has an "opposite" or a "reverse" polarity (i.e., reversed synthesis direction) relative to the orientation of the first, or of other nucleotide(s) N in the oligonucleotide sequence. Moreover, an oligonucleotide sequence comprising a mixture of polarities further comprises at least one (3'→3') or (5'→5') homogenous inverted polarity linkage.

Figure 5:
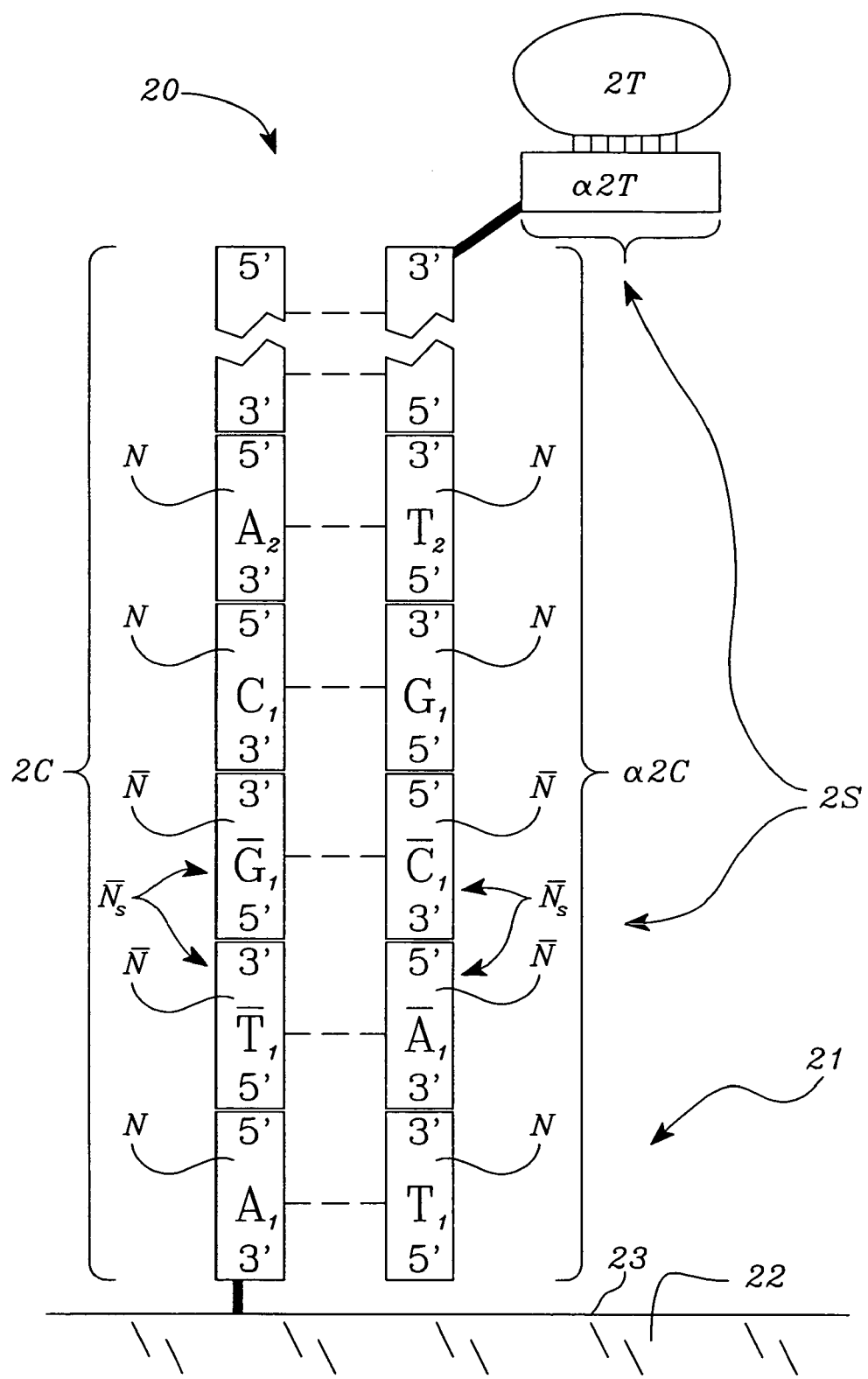
FIG. 5 is a magnified view illustrating the preferred embodiment of the system having specificity and sensitivity of the present invention after an assay.

FIG. 5 illustrates an example of the preferred embodiment of the present invention utilizing reverse polarity nucleotides $\overline{N}$ in an oligonucleotide capture probe 2C and oligonucleotide anti-capture α2C region of a solution probe 2S of system 20. The capture probe 2C is attached to the surface 23 of the substrate 22. For simplicity, only five nucleotides of the capture probe 2C and anti-capture region α2C are shown in some detail for the purposes of the following discussion. The first nucleotide of the oligonucleotide sequence illustrated in FIG. 5 is nucleotide $A_1$. This first nucleotide $A_1$ has the conventional 5'→3' orientation, that is, the 5' end of the nucleotide $A_1$ is "up" and is ready for synthesis in the conventional 5'→3' direction. Whether any other nucleotide in the sequence has a reversed polarity will depend on whether the orientation of the other nucleotide(s) is the same or reversed relative to the orientation of nucleotide $A_1$. The second nucleotide $T_1$ has a 3=→5' synthesis orientation. Therefore, nucleotide $\overline{T}_1$ has a reversed polarity relative to the polarity of the oligonucleotide sequence. Moreover, nucleotide $G_1$ has a 3'→5' orientation. Therefore, nucleotide $\overline{G}_1$ also has a reversed polarity orientation relative to the orientation of nucleotide $A_1$. The next two nucleotides, $C_1$ and $A_2$, have 5'→3' orientations, and therefore, have the same orientation as the first nucleotide $A_1$ of the oligonucleotide sequence.

The reversed polarity nucleotides $\overline{N}$ may be grouped together and/or interspersed throughout the oligonucleotide sequence between the same polarity nucleotides N, as is further discussed below. A reverse polarity nucleotide segment ($\overline{N}$s) comprises a group or sequence of s adjacent reverse polarity nucleotides $\overline{N}$. wherein s is one or more nucleotides $\overline{N}$. The segment ($\overline{N}$s) further comprises either a (3'→3') or a (5'→5') inverted polarity linkage at one end of the segment ($\overline{N}$s) that links with a same polarity nucleotide N. If the segment ($\overline{N}$s) is linked at the other end by a same polarity nucleotide N, then the segment ($\overline{N}$s) will further comprise the other of the inverted polarity linkages at that end of the segment. FIG. 5 illustrates the segment ($\overline{N}$s) of $\overline{T}_1$-$\overline{G}_1$ in the oligonucleotide probe 2C bounded by same polarity nucleotides $A_1$ and $C_1$. Therefore, the segment ($\overline{N}$s) has both (3'→3') and (5'→5') inverted polarity linkages at either end of the segment ($\overline{N}$s).

Also illustrated in FIG. 5 is the complementary solution probe 2S of the system 20. The complementary anti-capture region α2C of the solution probe 2S is hybridized to the capture probe 2C in the conventional anti-parallel relationship. Since the capture probe 2C has been defined above as being in a 5'→3' synthesis orientation, the anti-parallel complementary anti-capture region α2C is by definition in the 5'→3' synthesis orientation, starting at the anti-target region α2T through $T_1$ of the anti-capture region α2C. The nucleotides $T_1$, $G_1$, and $T_2$ of the anti-capture oligonucleotide sequence region α2C have a 5'→3' synthesis orientation and therefore, are same polarity nucleotides N. The nucleotides $T_1$, $G_1$, and $T_2$ are hybridized to same polarity nucleotides, $A_1$, $C_1$, and $A_2$ in the capture sequence 2C, respectively. The nucleotides $\overline{A}_1$ and $\overline{C}_1$ in the anti-capture sequence α2C both have a 3'→5' synthesis orientation and therefore, are reversed polarity nucleotides. The reverse polarity nucleotides $\overline{A}_1$ and $\overline{C}_1$ are hybridized to the reversed polarity nucleotides $\overline{T}_1$ and $\overline{G}_1$ in the capture sequence 2C, respectively The reversed polarity nucleotides $\overline{A}_1$ and $\overline{C}_1$ in the anti-capture sequence region α2C also form a reversed polarity nucleotide segment ($\overline{N}s$) that is hybridized to the segment ($\overline{N}s$) in the capture probe 2C. The reversed polarity nucleotide segment ($\overline{N}s$) in the anti-capture sequence is bounded on either side by same polarity nucleotides N; thus, the segment ($\overline{N}s$) has both (5'→5') and (3'→3') inverted polarity internucleotide linkages at either end as illustrated in FIG. 5.

Also illustrated in FIG. 5 is an anti-target region α2T of the solution probe 2S in accordance with the invention. The anti-target region α2T is attached or linked to the anti-capture region α2C and independently to a respective target 2T as the result of an assay.

The number of total nucleotides, the number of reverse polarity nucleotides $\overline{N}$ or segments $\overline{N}s$ in the probes 2C, 2S shown in FIG. 5 are illustrative only and in no way is intended to limit the scope of the invention. The total number of nucleotides and number of reverse polarity nucleotides $\overline{N}$ or segments $\overline{N}s$ in the capture probes 2C and anti-capture regions α2C that are within the scope of the invention are described below.

The reverse polarity nucleotides $\overline{N}$ used in accordance with the invention are described in more detail in:

(1) M. Koga, M. Moore and S. Beaucage, "Alternating α,β-Oligothymidylates with Alternating (3'→3')- and (5'→5')-Internucleotidic Phosphodiester Linkages as Models for Antisense Oligodeoxyribonucleotides", *The Journal of Organic Chemistry*, 1991, Volume 56, No. 12, pp. 3757-3759;

(2) M. Koga, S. Geyer, J. Regan and S. Beaucage, "The synthesis of alternating α,β-oligodeoxyribonucleotides with Alternating (3'→3')- and (5'→5')-Internucleotidic Linkages as Potential Therapeutic Agents", *Nucleic Acids Symposium Series*, No. 29, 1993, pp. 3-4; and (3) M. Koga, A. Wilk, M. Moore, C. Scremin, L. Zhou, and S. Beaucage, "Synthesis and Physiochemical Properties of Alternating α,β-oligodeoxyribonucleotides with Alternating (3'→3')- and (5'→5')-Internucleotidic Phosphodiester Linkages", *J. Org. Chem.*, 1995, 60, 1520-1530, each of which is incorporated herein by reference.

A nucleotide with reversed polarity $\overline{N}$ in an oligonucleotide sequence hybridizes preferentially with another reverse polarity complementary nucleotide $\overline{N}$, because the bond is thermodynamically more stable than a bond between a reversed polarity nucleotide $\overline{N}$ and a complementary non-reversed polarity nucleotide N. The hybridization bond stability is measured as a function of denaturation temperature "Tm". The inverted polarity (3'→3') and (5'→5') linkages at either end of the reverse polarity nucleotide $\overline{N}$ or segments $\overline{N}s$ are believed to have different internucleotide bond-lengths when compared with the conventional (3'→5') and (5'→3') linkages and this disparity in internucleotide distances impairs the hybridization between reverse polarity $\overline{N}$ and non-reversed polarity nucleotides N (see References (2) and (3) above).

For the purpose of emphasizing the thermodynamic effect that the reverse polarity nucleotides $\overline{N}$ have in providing good specificity and sensitivity of the system 20 in accordance with the invention, some of the evaluation and results reported by M. Koga et al. in References (2) and (3) are summarized below. The denaturation temperatures (Tm's) were evaluated and reported by M. Koga et al. for the hybridization of reversed polarity oligomers having 24 nucleotides in length (α,β-oligonucleotides) that were complementary to an unmodified region overlapping the splice acceptor site of the second exon encoding the HIV-1 Tat gene product. The α,β-deoxy-oligonucleotides had alternating (3'→3') and (5'→5') phosphodiester internucleotide linkages ("modified d-oligomers$_{24}$"). The complementary unmodified deoxy-oligonucleotides comprised only natural (5'→3') phosphodiester linkages ("natural d-oligomers$_{24}$"). The different combinations of natural and modified deoxy-oligomer duplexes are reproduced as No. 1-3 in Table 2 below. Also evaluated and reported by M. Koga et al. were the Tm's for the ribo-oligonucleotides ("natural r-oligomer $_{24}$") hybridized with the modified and natural d-oligomers$_{24}$. The Tm's of the deoxy- and ribo-oligomer duplexes also are reproduced in No. 4-5 in Table 2 below.

TABLE 2

Tm of Natural and Modified Polynucleotide Duplexes (Information herein is reproduced in part from Table 1 of Ref. 2 (for No. 1, 2, 3 below) and Table 3 of Ref. 3 (for No. 4, 5 below))

| No. | Duplex | Tm | Δ |
|---|---|---|---|
| 1 | natural d-oligomer$_{24}$ - natural d-oligomer$_{24}$ | 67° C. | — |
| 2 | modified d-oligomer$_{24}$ - natural d-oligomer$_{24}$ | 53° C. | −14° C. |
| 3 | modified d-oligomer$_{24}$ - modified d-oligomer$_{24}$ | 61° C. | −6° C. |
| 4 | natural d-oligomer$_{24}$-natural r-oligomer$_{24}$ | 62° C. | — |
| 5 | modified d-oligomer$_{24}$-natural r-oligomer$_{24}$ | 35° C. | −27° C. |

The denaturation temperatures are 14 degrees lower for duplexes of "natural-modified" oligonucleotide duplexes (No. 2) than for the "natural-natural" oligonucleotide duplexes (No. 1), which indicates a lack of stable hybridization or binding between complementary natural and reverse polarity nucleotides. However, the Tm for the duplex of "modified-modified" oligonucleotides (No. 3) was 8 degrees higher than the "natural-modified" oligonucleotides (No. 2) and only 6 degrees lower than the "natural-natural" oligonucleotide (No. 1), which indicates that the hybridization bonds are stronger and thermodynamically more stable for the "modified-modified" nucleotides than their "modified-natural" oligonucleotide counterparts. Therefore, the reversed polarity nucleotides $\overline{N}$ of the system 20 will be less likely to cross-hybridize with other complementary nucleotides N having non-reversed polarity. Advantageously, the reversed polarity nucleotides $\overline{N}$ of the system 20 will be even less likely to cross-hybridize with noncomplementary or "mismatched" nucleotides N. The chemically modified nucleotides $\overline{N}$ effectively preferentially hybridize with complementary similarly modified nucleotides $\overline{N}$.

The effect is believed to be more disruptive to cross-hybridizations than would be observed from a natural or non-reversed polarity nucleotide N mismatch, as provided in the conventional methods of minimizing cross-hybridizations (see Brenner references). Thus, cross-hybridization between a sequence containing a reversed polarity nucleotide $\overline{N}$ or segment $\overline{N}s$, in accordance with the invention, and a non-reversed polarity nucleotide N or sequence Ns, such as those also present in the capture probes 2C, anti-capture regions α2C, anti-target regions α2T and target samples 2T of the present invention, is less likely to occur. Advantageously, intramolecular structures, such as hairpins, are also less likely to occur, rendering the system 20 of the present invention a powerful and robust tool for diagnostic biological assays.

The reversed polarity nucleotides $\overline{N}$ can be obtained as phosphoramidite derivatives, for example, from Glen Research of Sterling, Va. As mentioned above, the capture probes 2C and probe regions α2C of the solution probes 2S can be synthesized with any synthesis method and preferably, are synthesized in accordance with conventional oligonucleotide synthesis methods. Advantageously, the phosphoramidite derivatives $\overline{N}$ are incorporated into the oligonucleotide sequence using these conventional methods.

For the invention, the total length or number (L) of monomers (including both unmodified monomers and modified monomers M) in the capture probes 2C and anti-capture regions α2C of the solution probe 2S is sufficient enough to form strong hybridizations or binding between complementary capture probe 2C and anti-capture regions α2C to withstand the conventional stringent washing steps after hybridization. Preferably, the total number or length L of the capture probes 2C and anti-capture regions α2C of the solution probes 2S may be anywhere from 5 to 50 monomers, more preferably 10 to 30 monomers in length L, and even more preferably, between 10 to 25 monomers in length L.

In each of the capture probes 2C and anti-capture regions α2C of the solution probes 2S illustrated in FIG. 5 of the preferred embodiment, two reversed polarity nucleotides $\overline{N}$, (or one reverse polarity segment $\overline{N}s$), are shown for illustrative purposes only. In accordance with the invention, the number of modified monomers present in a capture probe 2C and solution probe 2S should be high enough to provide a reduced likelihood of cross-hybridizations and intramolecular structures, but not too high so that the number of modified monomers does not impact the synthesis yield of the capture probes 2C or anti-capture regions α2C. The number of modified monomers in a particular capture probe 2C and anti-capture sequence α2C can be readily determined empirically, without undue experimentation by one skilled in the art, and depends on the synthesis method chosen.

Generally, there may be anywhere from one to (L−1) modified monomers M, where L is the length of (or total number of overall monomers in) the respective capture probe 2C or anti-capture region α2C; or preferably, from 1 to (⅔)L modified monomers M; and more preferably, (¼)L to (½)L modified monomers M in the capture probes 2C and anti-capture regions α2C of the solution probes 2S. The modified monomers M can be interspersed in the probe individually (s in $\overline{N}s=1$), or interspersed in groups or segments (where s>1), as mentioned above. When the modified monomers M are interspersed in a regular pattern, for example, every other one, the number of inverted polarity linkages are advantageously maximized. A high number of inverted polarity linkages is advantageous, since these linkages disrupt cross-hybridizations and intramolecular structures, as discussed above. However, the number of available unique sequence combinations is more limited. If the modified monomers are interspersed in a random pattern, for example, there are more available unique sequence combinations. If the modified monomers are grouped together in one or more segments, the number of inverted polarity linkages is not maximized and there are relatively fewer available unique sequence combinations. One skilled in the art is able to determine the optimum distribution of modified monomers in a sequence in accordance with the invention.

According to a preferred embodiment, a capture probe 2C, and anti-capture region α2C can be designed with modified monomers M in accordance with the invention using the following formula: x=L−6−D, where x equals the maximum number of modified monomers M in the probe or region; L equals the length or total number of monomers of the probe or region; and 6 is the total number of monomers from the two ends of the probe or region before a modified monomer is inserted. For the preferred oligonucleotide embodiment, the number 6 represents the total of three nucleotides adjacent to the 3' end and three nucleotides adjacent to the 5' end of the oligonucleotide probe or region, because empirical results show that the last three nucleotides on the 3' end and on the 5' end are not as involved in specificity. That is, mismatches on the ends are not as disruptive as in the middle of the probe. Further, D equals the number of locations that a modified monomer M should differ in each of the probes or regions of a set. It is preferred that the locations of the reversed polarity nucleotides $\overline{N}$ or nucleotide segments $\overline{N}s$ in any 2 oligonucleotide probes of the same set should differ in at least D=2 positions to minimize hybridizations between noncomplementary reversed polarity nucleotides $\overline{N}$. The maximum number x of modified monomers M in a L=24 monomer length capture probe 2C and anti-capture region α2C, for example, would have at most x=24−6−2=16 chemically modified monomers M, located in positions $p_4$ to $p_{21}$ of the total positions $p_1$ to $p_{24}$ of the 24 monomer long polymer. Preferably, there are a minimum of two (2) modified monomers M in any probe or anti-capture region of the invention. Moreover, it is preferred that the chemically modified monomers M be dispersed throughout the length of the probe 2C, and region α2C, rather than grouped together in one location on each and more preferably, dispersed in a random pattern. One skilled in the art would know how to disperse the chemically modified monomers M throughout the probe or region length L to achieve optimum results.

Also, as mentioned above, there should be a sufficient number of monomers in the probe and region sequences such that the hybridization between a capture probe 2C and an anti-capture region α2C is strong enough to withstand the stringent well-known washing steps, so that the respective assembled target 2T remains assembled to the apparatus 21 via the solution probe 2S. The capture probe 2C and anti-capture region α2C may each further comprise a member of a specific binding pair Y-Z. The specific binding pair Y-Z is cross-linked with a covalent bond or a strong non-covalent interaction that will withstand the stringent washing steps and help to hold the hybridized capture probes 2C and anti-capture regions α2C together. The strong bond between the cross-linking pair Y-Z is formed using, for example, a chemical catalyst or photo-reactive chemistry with illumination. The specific binding pair Y-Z of this embodiment would have to be of a type that did not interfere with the base pairing and base-stacking of its neighboring monomers in the sequence.

Figure 6:
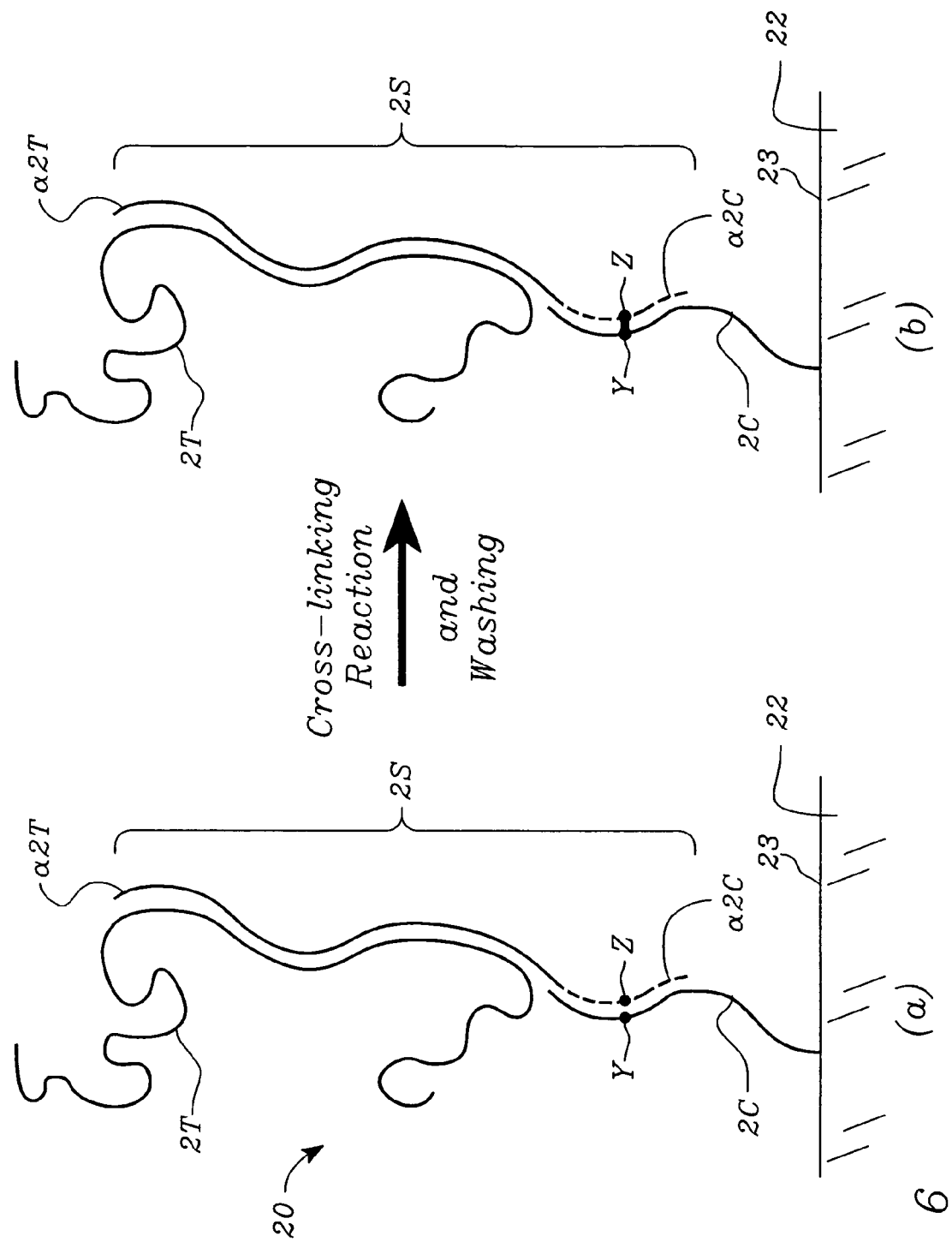
FIG. 6 is a diagram illustrating another embodiment of the system having specificity and sensitivity of the present invention comprising a cross-linking monomer pair.

FIG. 6 illustrates the specific binding pair Y-Z in this embodiment of system 20. Capture probe 2C, containing the binding member Y, is hybridized to the anti-capture region α2C, containing the binding member Z, of solution probe 2S. Solution probe 2S is also hybridized or bound to a target 2T at the anti-target region α2T, as illustrated in part (a) of FIG. 6. The members Y and Z are cross-linked, resulting in Y-Z linked pair, as illustrated in part (b) of FIG. 6. The cross-linked pair Y-Z provides further assurance that capture probe 2C retains its hybridization bonds to the solution probe 2S after the stringent washing step, and therefore, that only the specific binding of the appropriate target 2T to the respective solution probe 2S is subsequently measured or analyzed. As a result, this embodiment provides stronger bonds between respective capture probe 2C and anti-capture region α2C, and is especially useful in embodiments where relatively short capture probes 2C and anti-capture regions α2C (i.e., less than 15-monomers in total length L) are desired, but are not able to provide enough hybridization bonds, in the absence of such cross-linking, to withstand the stringent washing steps after the hybridization steps.

The capture probes 2C and anti-capture regions α2C monomer sequences may further comprise other monomers, such as polyethylenes or protein-nucleic acid PNA hybrids, to serve as spacers in the monomer sequences. These spacers are added to the capture probes 2C and anti-capture regions α2C using conventional phosphoramidite or nonphosphoramidite techniques, for example. The use of spacers is well known in the art for achieving length without specificity, to minimize cross-hybridizations, to distance a reaction from the surface of a substrate and/or to decrease cost, for example. The above uses are illustrative and in no way intended to limit the scope of the invention. There are many other uses for spacers not mentioned here that are readily apparent to one skilled in the art. All of which are within the scope of the invention.

The present system 20 with good specificity and sensitivity is particularly useful in sandwich hybridization assays on arrays and provides a powerful feature to the system 10 and method 30 for multiplexing one or more samples, having one or more targets per sample, on a single array.

In the preferred embodiment, an array assay system 20" having good specificity and sensitivity for such multiplexing is provided. The preferred array system 20" differs from system 20 by comprising an array apparatus 21" that has the first set of probes 2C located on a substrate 22" in an array of features $24_{i=1 \rightarrow n}$, wherein a different capture probe $2C_i$, is located on a different feature location $24_i$ of the array apparatus 21". There may be multiple copies of each different capture probe $2C_i$, at each location. Each capture probe $2C_i$ in the set may be different by having a different sequence of monomers. As in system 20, the capture probes 2C comprise one or more chemically modified monomer(s) M and may comprise a member of cross-linking pair Y-Z and/or a spacer, in accordance with the invention.

Moreover, in accordance with this array assay system 20" embodiment, each solution probe $2S_{i,j}$, in the second set of probes 2S may be different by comprising a different anti-capture sequence region $\alpha 2C_i$ and either the same anti-target region $\alpha 2T_j$ or a different anti-target region $\alpha 2T_{j=1 \rightarrow m}$, depending on the biological materials to be assayed (i.e., the number of samples P and the number of targets 2T per sample). The anti-capture sequence region $\alpha 2C_i$ comprises one or more chemically modified monomer(s) M that are complementary to respective similarly modified monomers M in the capture probe $2C_i$ and may also comprise a member of a cross-linking pair Y-Z. There may be multiple copies of each different solution probe $2S_{i,j}$, in the set. The set of capture probes 2C provides an address for each target material $2T_{j,k}$ on the array and the set of solution probes 2S essentially assembles or delivers each target $2T_{j,k}$ to its corresponding capture probe location $2C_i$ during the array assay to provide an addressable and self assembling assay with good specificity and sensitivity.

Figure 7:
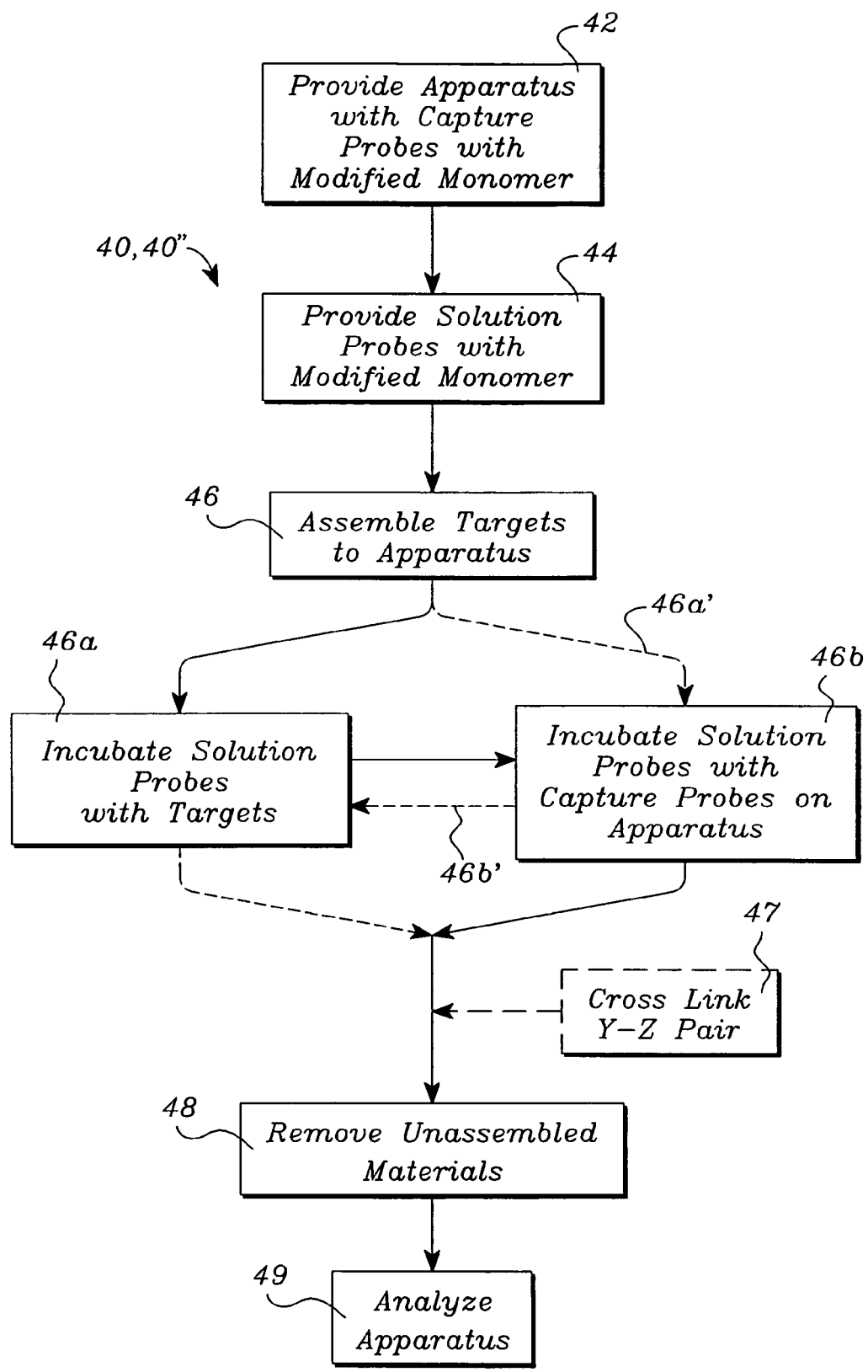
FIG. 7 is a block diagram illustrating the method of assaying having specificity and sensitivity in accordance with one embodiment of the invention.

A method 40 of assaying biological materials having good specificity and sensitivity according to the present invention is illustrated in FIG. 7. The assay method 40 comprises the steps of providing (42) the assay apparatus 21 having the first set of biological probes (capture probes 2C) comprised of a sequence of monomers attached to the substrate 22.

In the preferred embodiment, an array assay method 40" is performed using the array apparatus 21". Therefore, in the preferred embodiment, the set of capture probes 2C are attached to the surface 23" of the array substrate 22" in an array of feature locations 24. There is a different probe $2C_i$ of the set at each different feature location $24_i$. Preferably, there are multiple copies of each different capture probe $2C_i$ at each feature location $24_i$.

The method 40, 40" further comprises the step of providing (44) the second set of biological probes (solution probes 2S), that comprises the first sequence region of monomers and a second region. The first sequence region (anti-capture region α2C) of the solution probes 2S is complementary to the monomer sequence on the capture probe 2C, and the second sequence region (anti-target region α2T) on the solution probes 2S is complementary to biological targets 2T to be assayed. In the preferred array assay embodiment, each solution probe $2S_{i,j}$, of the set of solution probes 2S comprises the first sequence region $\alpha 2C_i$ complement to a respective capture probe $2C_i$ of the array apparatus 21" and a second region $\alpha 2T_j$ complement to a respective target $T_j$ in a respective sample $P_k$. Therefore, one or more biological samples $P_k$, having one or more biological targets $2T_j$, per sample, can be assayed together (multiplexed) on the same array apparatus 21".

Each capture probe $2C_i$ of the set of capture probes 2C comprises in the monomer sequence one or more monomer(s) M having a chemical modification. Each first sequence region α2C of the set of solution probes 2S comprises one or more respective complementary monomer(s) M having a similar chemical modification, wherein the complementary similarly modified monomers M in the capture probes 2C and the anti-capture sequence region α2C of the solution probe 2S will preferentially hybridize or bind to each other instead of to a complementary monomer that is not similarly modified (also referred to as an "unmodified monomer").

When the capture probes 2C and anti-capture regions α2C of the solution probes 2S comprise oligonucleotides, as in species 1-5, 10 and 11 of Table 1, the monomer sequence of the capture probe 2C and the anti-capture monomer sequence region α2C each comprises complementary reversed polarity nucleotides $\overline{N}$ relative to the polarity of the respective monomer sequence, as defined above by the first nucleotide in the sequence. As stated above for the preferred embodiment of the system 20, "preferentially hybridize or bind to each other" means that the reversed polarity nucleotide $\overline{N}$ forms a thermodynamically more stable hybridization with another complementary reversed polarity nucleotide $\overline{N}$ than with non-reversed polarity nucleotide N.

The method 40, 40" of assaying biological materials further comprises the step of assembling (46) the target materials 2T to the substrate 22, 22" for evaluation. The target materials 2T are linked indirectly or assembled to the apparatus 21, 21" similarly to the method 30 described above. The hybridizations may be performed simultaneously or preferably, in steps. In the first hybridization step 46a, the targets 2T are pre-incubated with the solution probes 2S to allow the binding or hybridization to occur in solution phase between the targets 2T and the anti-target regions α2T of the solution probes 2S. The concentration of solution probes 2S is preferably the same as that for method 30. After the pre-incubation step (46a), the hybridized {target-solution probe} species in solution is incubated with the apparatus 21, 21" of capture probes 2C on the substrate 22, 22" for hybridization or binding between the capture probes 2C and the anti-capture regions α2C of the hybridized {target-solution probe} species to occur (step 46b). Alternatively, the hybridization steps can be reversed, but like the simultaneous hybridizations, the advantages of hybridizing the solution probes with the target in solution are not available. When the hybridizations steps are reversed, the solution probes 2S can be pre-incubated with the capture probes 2C on the apparatus 21, 21" (step 46b' dashed arrow in FIG. 7). Then the targets 2T are added to the {capture probes-solution probes} system 20, 20" for binding to the anti-target region α2T of the solution probes 2S (step 46a' dashed arrow in FIG. 7). In all situations, the hybridization or binding is performed under well-known conditions in the art. However, the simultaneous hybridizations and the reversed hybridization steps 46b', 46a' are not recommended where the assay involves one or more biological target(s) $2T_j$, $k$ in more than one biological sample $P_{k=1\ to\ x}$, because of the need to keep the samples separated until the solution probes 2S are hybridized with respective targets 2T in the respective samples P.

The method 40, 40" further comprises the step of removing (48) the unhybridized/unbound material from the incubated apparatus 21, 21" by washing the apparatus 21, 21" using conventional materials and processes; and the step of analyzing (49) the results of the assay, according to conventional methods. At some point during the assay, a labeling system is added to either the target samples 2T, capture probes 2C, solution probes 2S or the like, that produces a signal when interrogated during the analysis step 49. Preferably, the label produces an optical signal that is detected optically with conventional optical scanning equipment, however other labels and detection methods are applicable to the invention. The labeling system, its introduction into the assay, and the method of detection are not the subject of the present invention. Any conventional labeling and detection techniques, materials and equipment can be used. The hybridized system 20, 20" is analyzed (49) to track, sort, identify and further characterize the targets 2T using conventional equipment.

However, when the capture probes 2C and solution probes 2S comprise the cross-linking pair Y-Z, before the step of removing (48), the method 40, 40" further comprises the step of cross-linking (47) the monomer pair Y-Z on the capture probes 2C and solution probes 2S, respectively, to strengthen the bond or hybridization between the capture probes 2C and respective anti-capture region α2C on the solution probes 2S to better withstand the stringent washing step (48). The step of cross-linking 47 is illustrated in FIG. 7 via dashed box and arrow. In the step of cross-linking 47, preferably, the apparatus 21, 21" is first washed with a conventional low stringency wash procedure before the specific binding pair is cross-linked. The Y-Z specific binding pair will cross-link with a covalent bond or a strong non-covalent bond under appropriate conditions, such as photo-activation and/or chemical catalytic activation after the low stringency wash.

As mentioned above, the assay system 20, 20" and method 40, 40" of the present invention are advantageously useful for sandwich hybridization assays, and in particular in sandwich hybridization assays on arrays 21". The system 20, 20" and method 40, 40" provide specific and sensitive powerful assay tools for multiplexing one or more sample(s), having one or more target(s) per sample, and that are addressable and self-assembling, as in system 10 and method 30, described above. The solution probes 2S are customized for respective targets 2T in respective samples P and customized for respective capture probes 2C on the array apparatus 21". The solution probes 2S will bind or hybridize to the respective targets 2T and bind or hybridize to respective capture probes 2C with good specificity and sensitivity due to the preferential hybridization between complementary similarly modified monomers M. Therefore, the system 20, 20" and method 40, 40" provide good accuracy to the assay, which renders them particularly advantageous for multiplexing a plurality of different samples P, each sample $P_k$ having a plurality of different targets $2T_j$ per sample, on the same array 21".

Figure 8A:
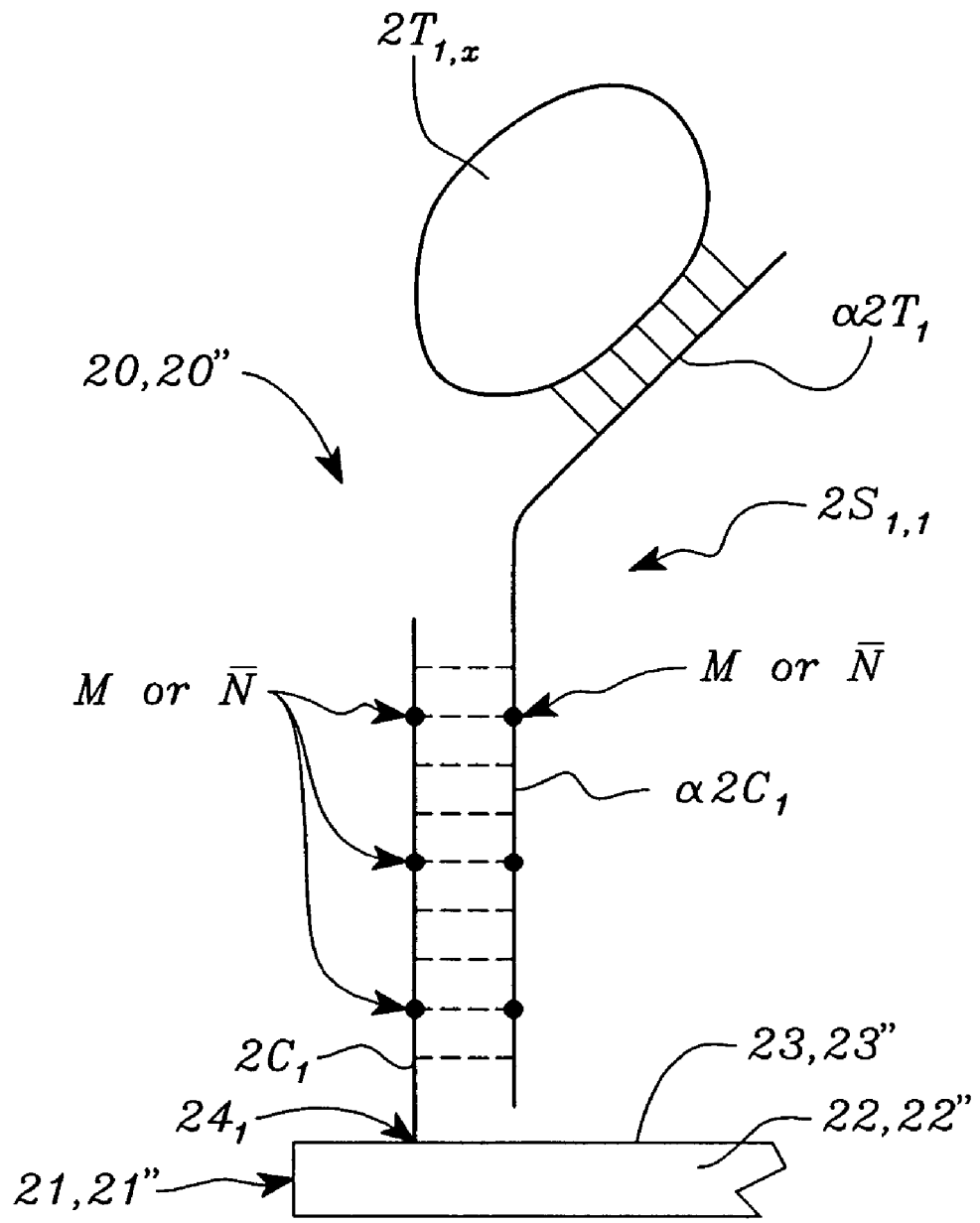
FIG. 8A is a diagram of the system having specificity and sensitivity after an assay illustrating a correct hybridization between respective probes and sequence regions of the invention and a target sample.
Figure 8B:
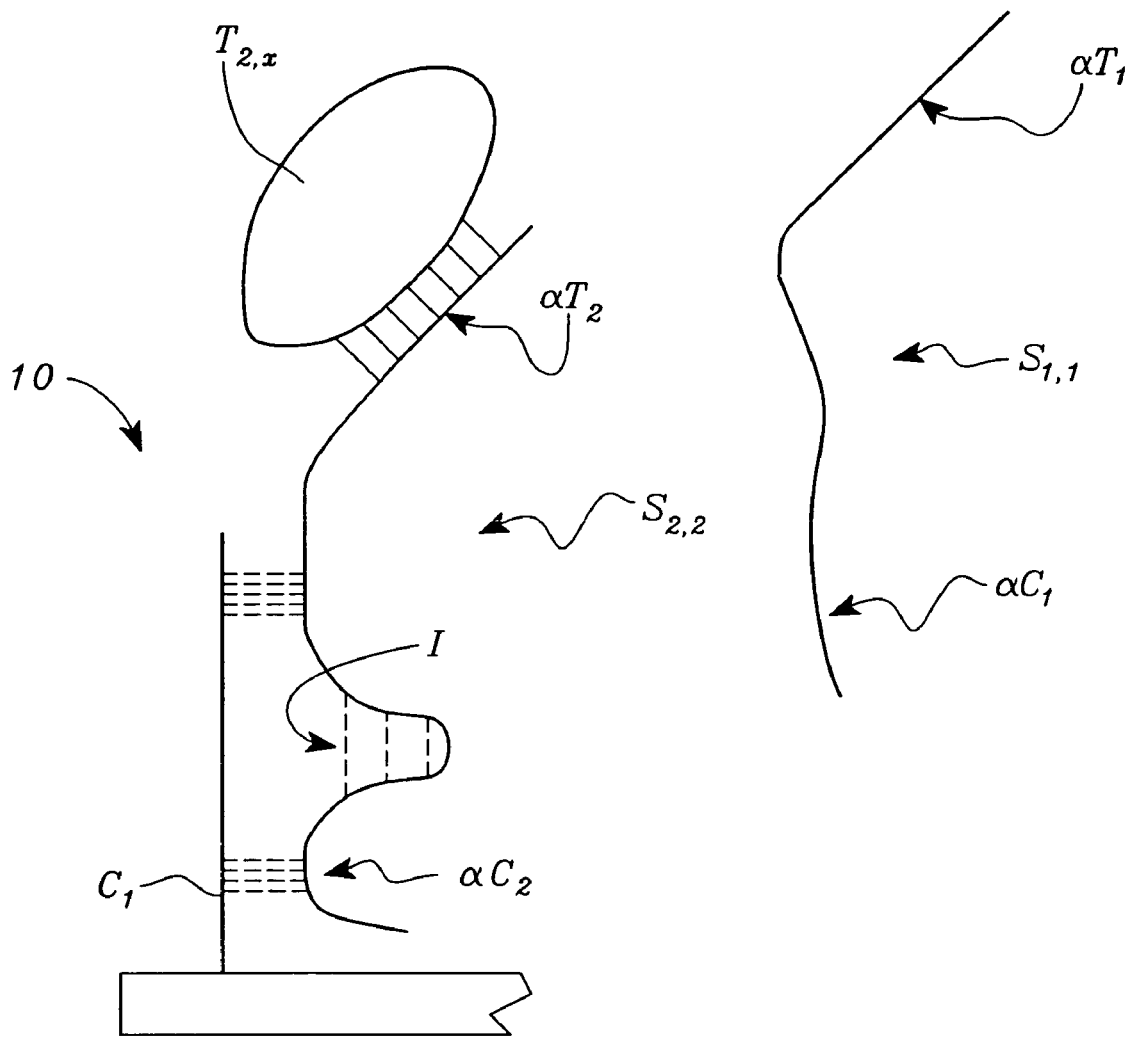
FIGS. 8B, 8C and 8D are diagrams of the system for multiplexing after an assay illustrating possible cross-hybridizations and intramolecular structures.
Figure 8C:
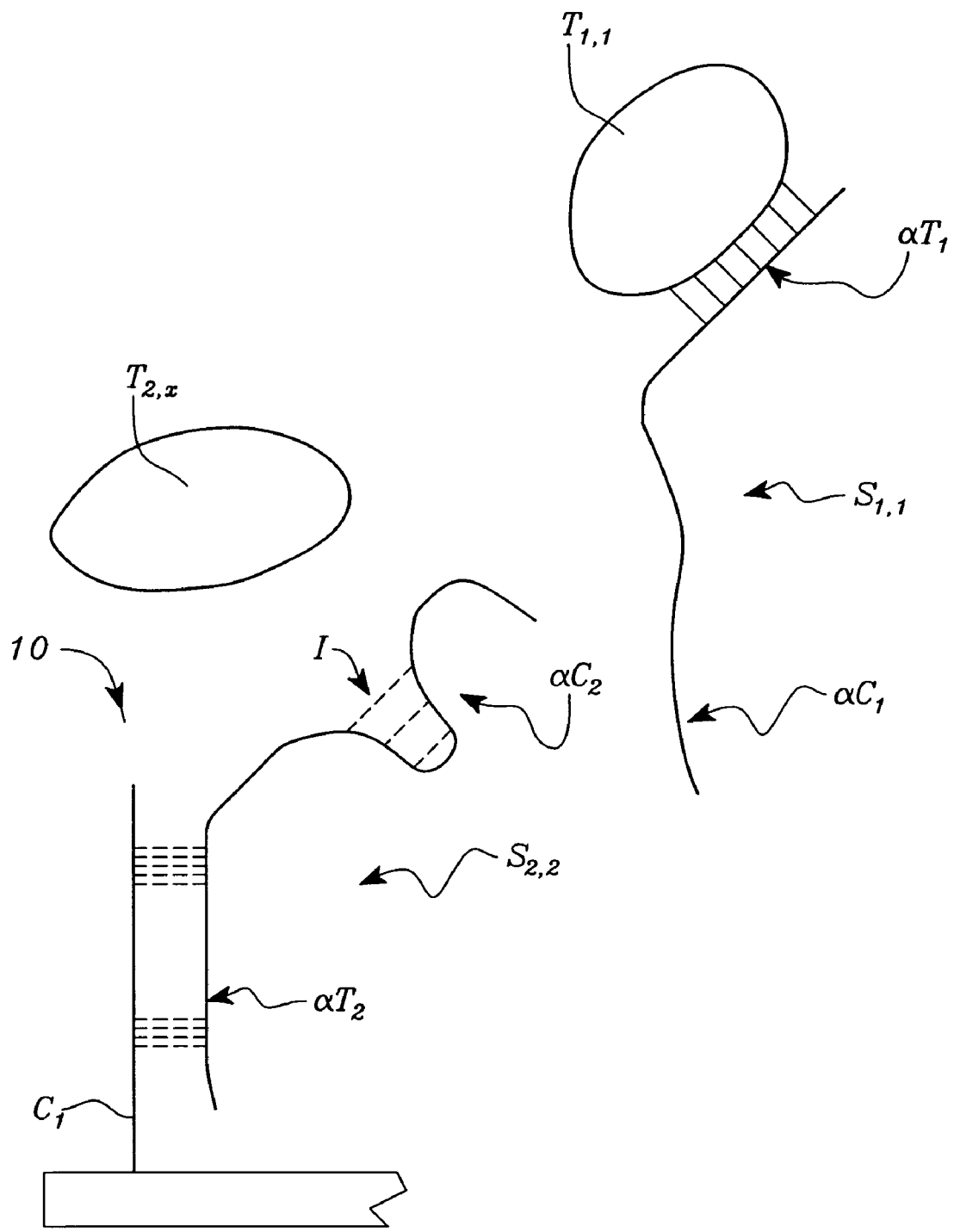
Figure 8D:
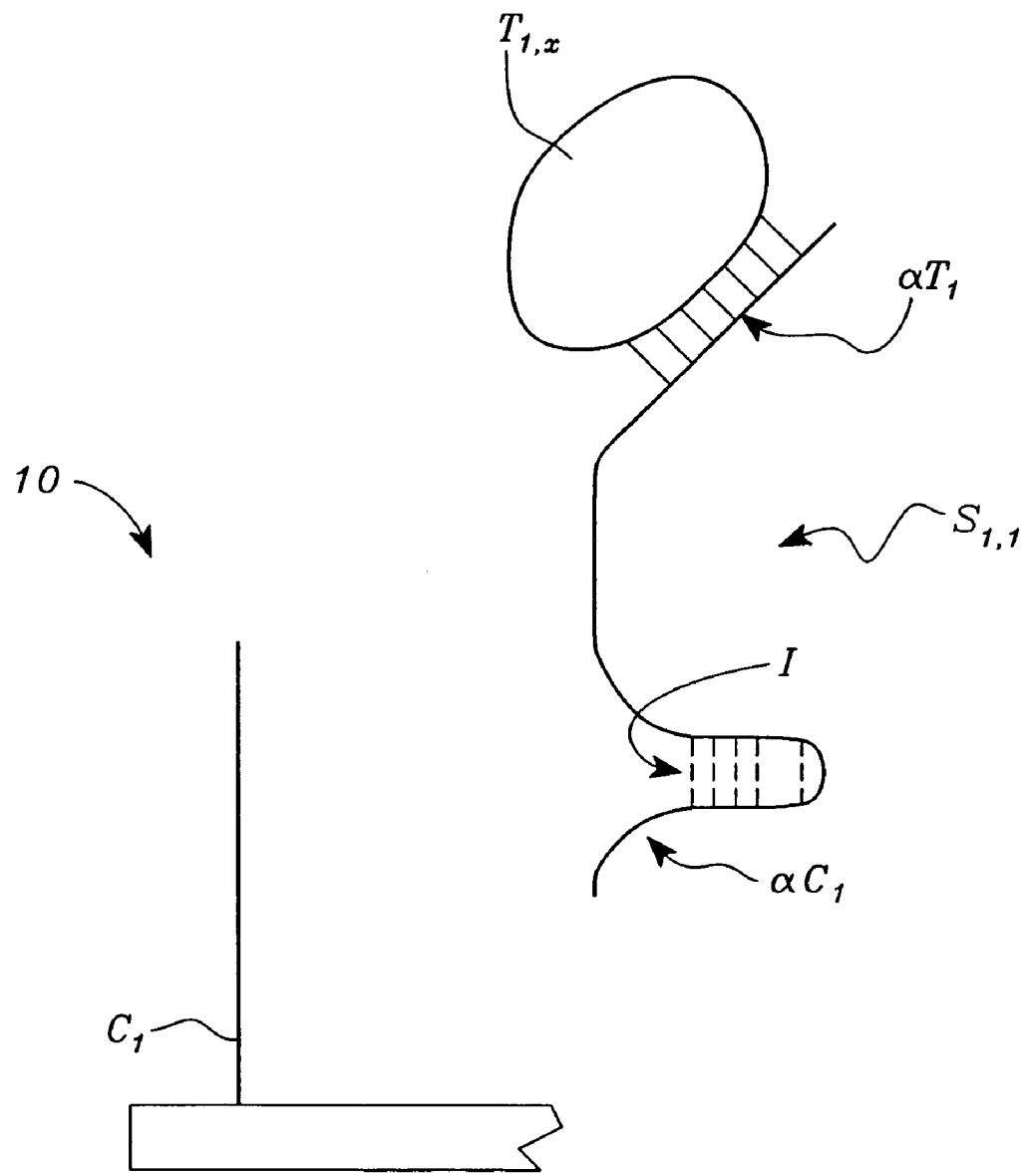

The system 20, 20" and method 40, 40" with complementary modified monomers M provide many advantages, at least three are described below. First, the complementary modified monomers M provide good specificity to the assay by systematically providing a reduced likelihood of undesired hybridizations from occurring that are likely reduced relative to system 10 and method 30. The likelihood of undesired hybridization is reduced because the modified monomers M preferentially hybridize to each other instead of with a complementary unmodified monomer. For the preferred embodiment, the hybridization preference of reversed polarity nucleotides A with each other is due to the disruptive effects of the different internucleotide linkage distances of the reversed polarity nucleotides N and non-reversed polarity nucleotides N. FIG. 8A illustrates one example of a correct hybridization in accordance with the system 20, 20" of the present invention. FIGS. 8B and 8C illustrate two scenarios having mismatched cross-hybridizations and FIG. 8D illustrates an intramolecular structure. These figures illustrate problems that are typical in conventional sandwich hybridization assays and which may occur in the system 10 and method 30 for multiplexing of the invention described above, when modified monomers M are not included to provide good specificity and sensitivity.

FIG. 8A illustrates a portion of apparatus 21, 21" comprising a particular capture probe $2C_1$ located at feature 241 on the surface 23, 23" the substrate 22, 22". The capture probe $2C_1$ has three (3) modified monomers M, or in the preferred embodiment, reversed polarity nucleotides $\overline{N}$, illustrated by way of example only. The capture probe $2C_1$ is hybridized to its complementary anti-capture region $α2C_i$ of solution probe $2S_{1,\ 1}$. The solution probe 2S1, 1 further comprises an anti-target region $α2T_1$ that is complementary and hybridized to a target $2T_{1,\ x}$ from an arbitrary sample $P_x$, not shown.

Symbolic discrimination and other screening methods are typically employed in conventional systems to minimize cross-hybridizations. As mentioned above, Brenner discloses one method of symbolic discrimination by introducing at least two mismatched pairs into the polynucleotide tags. Other methods of screening are described in EP 0 799 897 $A_1$ (D. Schoemaker) published Oct. 8, 1997 and U.S. Pat. No. 5,556,749 (Mitsuhashi et al.) issued Sep. 17, 1996, among others, all of which are incorporated herein by reference. Each of these methods and others not listed here would work to screen the capture probes C and anti-capture regions αC of system 10 to produce "minimally cross-hybridizing sets". These methods of screening would work on the capture probes 2C and anti-capture regions α2C of system 20 as well. However, the conventional screening methods are not entirely successful in preventing the problem of cross-hybridizations and some do not address the problem associated with intramolecular structures, which affect the assay specificity and sensitivity, respectively.

Advantageously, the system 20, 20" and method 40, 40" systematically provide a reduced likelihood of cross-hybridizations and intramolecular structures even before the probes 2C and regions α2C are screened according to any of the conventional methods. In fact, the system 20, 20" and method 40, 40" of the present invention are more likely to prevent mismatches between complex targets and the capture probe 2C or anti-capture region α2C during an assay. The conventional screening methods are not able to screen for mismatches with complex targets, because complex targets are difficult to screen, especially when the sequences of the target material is not known or not known completely or with certainty. Consider a target 2T comprised of RNA, for example, and the respective capture probes 2C and anti-capture regions α2C of the solution probes 2S used in the assay, each comprising complementary reversed polarity deoxyribonucleotides $\overline{N}$ in their sequences. According to Table 2 above, advantageously, a mismatch between complementary ribonucleotides of the RNA target and the deoxyribonucleotides $\overline{N}$ of the capture probes 2C and regions α2C are even less likely to occur, due to the more disruptive effects of the different internucleotide linkage distances of the reversed polarity deoxyribonucleotides $\overline{N}$ with respect to non-reversed or "natural" ribonucleotides of the target. The more disruptive effects are shown by the ΔTm for No. 5 of Table 2, which is −27° C. for the modified d-oligomer$_{24}$-natural r-oligomer$_{24}$ (almost twice as high as the ΔTm (−14° C.) for the modified/natural d-oligomers, No. 2). This advantage of the present system 20, 20" and method 40, 40" is evident even when the capture probes 2C and anti-capture regions α2C are the oligoribonucleotides and comprise reversed polarity ribonucleotides $\overline{N}$ and the target to be assayed is a complex DNA, e.g., cDNA. Therefore, the present invention systematically provides a reduced likelihood of cross-hybridizations with the target 2T, which is something that conventional methods are unable to do.

FIG. 8B illustrates an example of a system 10 solution probe $S_{2,2}$ that is linked to an appropriate target $T_{2,x}$, from an arbitrary sample $P_x$, but its anti-capture region α$C_2$ has hybridized to the wrong capture probe $C_1$ on the substrate 12. The cross-hybridization (hybridization with mismatches) between the monomers of capture probe $C_1$ and the monomers of anti-capture region α$C_2$ prevents solution probe $S_{1,1}$, comprising the anti-target region α$T_1$ and the anti-capture region α$C_1$, from properly hybridizing to capture probe $C_1$. Since this example has no target $T_1$ in sample $P_x$, the incorrect presence of target $T_{2,x}$ at the $C_1$ address produces a false positive result in an assay for target $T_{1,x}$.

In FIG. 8C, the solution probe $S_{2,2}$ has cross hybridized with capture probe $C_1$, at solution probe $S_{2,2}$'s anti-target region α$T_2$, such that the solution probe $S_{2,2}$ is not able to bind to its appropriate target $T_{2,x}$, (arbitrarily from sample $P_x$). As a result, the solution probe $S_{1,1}$ with its appropriate target $T_{1,1}$ attached (arbitrarily from sample $P_1$) is blocked, by solution probe $S_{2,2}$, from correctly hybridizing with the capture probe $C_1$. This produces a false negative result for target $T_{1,1}$. The many different cross hybridizations (hybridization with mismatches) that occur in conventional systems, and that are possible in the multiplexing system 10 of the invention, are too numerous to describe all of them herein. The examples shown in FIGS. 8B and 8C are just illustrative of the types of cross-hybridizations that could occur. The present system 20, 20" and method 40, 40" systematically provide a reduced likelihood of these cross-hybridizations from occurring as a result of the good specificity introduced by the use of chemically modified complementary monomers M.

The system 20, 20" and method 40, 40" provide a reduced likelihood of hybridization mismatches between (1) capture probes 2C and sequences that are not complementary to the capture probes 2C, such as noncomplementary anti-capture sequences α2C of solution probes 2S, anti-target sequences α2T of solution probes 2S, or target sequences 2T; and (2) anti-capture sequences α2C and sequences that are not complementary to the anti-capture sequences, such as non-complementary capture probes 2C, other anti-capture sequences α2C, anti-target sequences α2T of solution probes 2S, or target sequences 2T. Minimizing the likelihood of cross-hybridizations enhances the specificity of the system 20, 20" and method 40, 40".

Second, the complementary modified monomers M of the system 20, 20" and method 40, 40" of the present invention provide a reduced likelihood of intramolecular structures forming within capture probes 2C and their complementary anti-capture sequences α2C. A reduced probability of intramolecular structures forming increases the sensitivity of the hybridization between the capture probes 2C and their complementary anti-capture sequences α2C. FIGS. 8D illustrates a solution probe, such as $S_{1,1}$ of the system 10, wherein an intramolecular structure I has formed within the anti-capture region α$C_i$ that hinders the proper hybridization between the complementary capture probe $C_1$ and the anti-capture region α$C_1$. The intramolecular structure causes a false negative for target $T_{1,x}$ (arbitrarily from sample $P_x$). System 20, 20" and method 40, 40" provide modified monomers M interspersed among the sequences of the capture probes 2C and anti-capture regions α2C. The binding of modified monomers M to complementary monomers that are not similarly modified is not favored thermodynamically. Thus, there is a reduced likelihood of intramolecular structures I forming within the capture probes 2C or within the anti-capture regions α2C. In the preferred embodiment, the reversed polarity nucleotides $\overline{N}$ systematically provides a reduced likelihood that intramolecular structures I will occur due to the disruptive effects of the different internucleotide linkage distances of the reverse polarity nucleotides $\overline{N}$ and the non-reversed polarity nucleotides N.

Third, the system 20, 20" and method 40, 40" having the complementary modified monomers M advantageously have more permutations of sequences for a given length of capture probe 2C and anti-capture region α2C. For example, in the preferred oligonucleotide capture probes 2C and anti-capture regions α2C of the solution probes 2S, the use of reversed polarity nucleotides $\overline{N}$ will allow more "letters" with which to make unique "words"; that is, there will be eight unique nucleotide bases, instead of four with which to design probes 2C and 2S. Thus, there are the four nucleotides A, T (U), C, and G with non-reversed polarity N and four nucleotides $\overline{A}$, $\overline{T(U)}$, $\overline{C}$ and $\overline{G}$ with reversed polarity $\overline{N}$ with which to form unique sequences in the capture probes 2C and anti-capture regions α2C of the solution probes 2S to generate unique probe sequences for an assay.

For example, if a probe is desired with a length of 20 nucleotides, then using the four non-reversed polarity nucleotide bases N, one can achieve $4^{20}$ ($=1.1E^{+}12$) combinations of sequences. If these combinations are screened to remove those combinations that are likely to cross-hybridize using the method described by Brenner or others, referenced above, to provide sequences with minimal cross-hybridization, then a far lower number of useful sequences is actually achieved. An even lower number would result with a secondary screening, using more rigorous criteria such as removing mismatch sequences that pass typical symbolic screenings but are filtered out using thermodynamic parameters of mismatches, such as that described in U.S. Pat. No. 5,556,749 (Mitsuhashi et al.) issued Sep. 17, 1996. An even lower number would result with a tertiary screening for intramolecular structures using conventional methods, such as that described by D. H. Mathews, T. C. Andre, J. Kim, D. H. Turner, and M. Zuker (1998) American Chemical Society Symposium Series 682, 246-257; N. B. Leontis and J. Santa Lucia Jr., eds., for example, and the references cited therein, all of which are incorporated herein by reference.

In contrast, the addition of the four reversed polarity nucleotides $\overline{N}$ with the four non-reversed polarity nucleotides N, as provided in the system 20, 20" and method 40, 40" of the present invention, provides a total of eight unique nucleotides $\overline{N}$, N. Each of the eight unique nucleotides $\overline{N}$, N can be used in each sequence position of the capture probe 2C example above having 20-nucleotides in length. Thus, there are $8^{20}$ ($=1.2E^{+}18$) combinations of sequences available. After conventional screening of these combinations for cross-hybridization and intramolecular structures, as above, a much larger set remains than would be possible with just the four natural or non-reversed polarity nucleotides N. In fact, the thermodynamic specificity that the complementary reversed polarity nucleotides $\overline{N}$ have for each other systematically provides a reduced likelihood that cross hybridizations and intramolecular structures will occur even before the sets are screened. Therefore, the number of useful sequence combinations for the system 20, 20" and method 40, 40" of the present invention is even larger and the length of the probes can be shorter. Shorter probe lengths advantageously have lower synthesis costs and faster turn-around time.

In fact, there are enough unique combinations of sequences using the reversed polarity nucleotides $\overline{N}$ of the present invention with the non-reversed polarity nucleotides N that probe lengths L as short as six nucleotides total comprising both reversed polarity nucleotides $\overline{N}$ and non-reversed polarity nucleotides N (collectively "$\overline{N}$, N") are possible. In a nucleotide probe length of L=6 nucleotides total example, one can achieve either $4^{\wedge}6(=4,096)$ conventional, or $8^{\wedge}6(=2.6E^{\wedge}+05)$ unique, combinations of sequences using either the 4 non-reversed N, or 8 reversed and non-reversed $\overline{N}$, N nucleotides, respectively. However, depending upon the washing stringency, the shortest oligonucleotide probe or region length L which has good hybridization strength is preferably L=15 total nucleotides $\overline{N}$, N for the system 20, 20" that includes a cross-linking pair Y-Z, and preferably, L=25 total nucleotides $\overline{N}$, N for the system 20, 20" without a cross-linking pair Y-Z.

For the sandwich hybridization assays on arrays, especially multiplexing array assays, as provided by the assay system 20" and method 40", there are preferably over 10,000 different capture probe 2C features to be supported with the possible sequence combinations. It should be apparent that the four non-reversed polarity nucleotide bases N provide a number of combinations after screening for minimal cross-hybridization and intramolecular structures that may be too low to support an array of over 10,000 features, depending upon the rigorousness of the screenings. To compensate for this inadequacy, the conventional systems would have to use progressively longer probe sequences to provide enough combinations after screening to support a large array of over 10,000 features. The longer the probe sequence, the more costly and less desirable the systems become.

Advantageously, a larger number of unique sequence combinations are available using the eight nucleotide bases $\overline{N}$, N, as provided by the system 20, 20" and method 40, 40" of the present invention, before and after screening for minimal cross-hybridizations and intramolecular structures. Therefore, the system 20, 20" and method 40, 40" of the present invention provide for sets of much greater than 10,000 capture probes 2C and anti-capture regions α2C for solution probes 2S that are unique with respect to each other and can be shorter than the conventional probe sequences. Advantageously, these sets of probes and sequence regions 2C and α2C are suitable for supporting the sandwich hybridization assay system 10 and method 30 for multiplexing well over 10,000 biological samples or biological targets on a single array. Thus, the capture probes 2C and complementary anti-capture sequences α2C of the system 20, 20" and method 40, 40" advantageously provide for probes 2C and sequence regions α2C that support arrays of over 10,000 features, that can be shorter in length, that have good specificity and sensitivity, and that are likely less costly to produce than the current state of the art. These capture probes 2C and solution probes 2S of system 20, 20" and method 40, 40" are readily adaptable for use with the multiplexing system 10 and method 30 of the invention.

As mentioned above, an important advantage of both systems 10, 20, 20" and methods 30, 40, 40" of the present invention is that customization of a sandwich hybridization assay resides in the preparation of the solution probes S, 2S, rather than in the preparation of the capture probes C, 2C bound to the apparatus 11, 21, 21". Therefore, manufacturing of the apparatus 11, 21, 21" will be more cost-effective and quicker due to the common or universal pool or set of capture probes C, 2C for all target biological material T, 2T and all samples P. The current state-of-the-art requires custom probes on an assay substrate, including an array substrate. In contrast, the assay apparatus 21, including the array apparatus 11, 21" can be fabricated in bulk and stored to allow cost savings compared to synthesizing custom probes on the apparatus of the conventional systems. The bulk fabricated apparatus 11, 21, 21" will have the generic set of capture probes C, 2C either synthesized in situ, or pre-synthesized and deposited, on the substrate 12, 22, 22". Moreover, the set of capture probes C, 2C of the invention can be synthesized in bulk and stored to allow cost savings compared to the cost of synthesizing different capture probes for each different type of custom assay. The pre-synthesized capture probes C, 2C can be spotted or chemically or enzymatically linked to the assay substrate 22 or to the appropriate feature location on the array substrate 12, 22" of the apparatus 11, 21, 21". In either case, large numbers of generic or universal assay apparatuses 21, including array apparatuses 11, 21" can be manufactured at a time, since the customization is in the solution probes S, 2S, thereby saving in cost and turnaround time for custom orders.

The kit, as mentioned above for system 10 and 30, can be provided with the system 20, 20" and written instructions for the method 40, 40". The kit provides sandwich hybridization assay capabilities to a user having good specificity and sensitivity, wherein such assay capabilities include multiplexing arrays, as provided by system 10 and 30.

The fabricated apparatus 11, 21, 21" of the invention is used to evaluate polynucleotide or oligonucleotide "target" samples to be tested. A user will expose the apparatus 11, 21, 21" to one or more samples, such as in hybridizing or binding assays, and interrogate the array following such exposure using well-known conventional methods. The interrogation will produce a result. Information about the target sample(s) can be obtained from the results of the interrogation. The user may be in a location remote to the location where the apparatus is fabricated. Moreover, the user may communicate the results or the information obtained from the results to a location remote to the user's location. A location is remote if it is at least a different location, e.g., a different building, a different city, different state or different country, or if the location is at least one, at least ten, or at least one hundred miles apart.

Another advantage of the present systems 10, 20, 20" and methods 30, 40, 40" of the invention is that the binding or hybridization between the target material T, 2T and the solution probe S, 2S (steps 36a, 46a) advantageously can occur in solution, as opposed to binding or hybridization on the surface 13, 23, 23" of the apparatus 11, 21, 21". Hybridization in solution advantageously allows for more effective kinetics of binding or hybridization, and more control over the temperature, mixing, and solution properties in the binding or hybridization step (36a, 46a). Since a particular target material T, 2T could be a large molecule, the anti-target sequence αT, α2T of the solution probe S, 2S may have to be a large molecule also, such as a cDNA, an antibody, etc., that is complementary to the large molecule target material T, 2T. A large anti-target sequence αT, α2T, having a large target molecule T, 2T attached, advantageously can be indirectly linked to the array apparatus 11, 21" through addressable, self-assembly described above, as opposed to current spotting techniques. Current spotting techniques can be accompanied by irreversible denaturation. The anti-target sequence αT, α2T of the solution probe S, 2S binds or hybridizes to the target T, 2T while in solution, so advanced instrumentation is not needed for the physical placement of molecules by micro-pipetting or masking of the array surface 13, 23" for example. In addition, the activity of the large molecules is easier to maintain in solution.

Moreover, the manufacture of the assay apparatus 11, 21, 21" used in the systems 10, 20 and methods 30, 40 of the present invention uses conventional materials and processes. The substrates 12, 22, 22" are made of glass, fused silica or clear plastics, and preferably siliceous glass (i.e. silica-based glass) is used in the invention because of its low intrinsic fluorescence. The siliceous glass can be obtained from Erie Scientific (Portsmouth, N.H.) or Corning (Corning, N.Y.). The capture probes C, 2C are either synthesized in situ directly onto the substrate 12, 22, 22" or pre-synthesized and deposited onto the substrate 12, 22, 22" as intact species, using conventional methods. The monomers are added to the substrate 12, 22, 22" using the technology concepts from the thermal ink jet printing systems made by Hewlett-Packard of Palo Alto, Calif., or piezoelectric printing systems, made by Epson of Japan, for example. The array apparatuses 11, 21" are manufactured using automated equipment, such that the spatial location on the substrate of each feature location is known within a certain margin of error.

Analysis (step 39, 49) of the assay is typically performed with commercially available optical scanning systems, examples of which are described in U.S. Pat. No. 5,837,475, U.S. Pat. No. 5,760,951 (confocal scanner) and U.S. Pat. No. 5,585,639 (off axis scanner), all incorporated herein by reference. Typical scanning fluorometers are commercially available from different sources, such as Molecular Dynamics of Sunnyvale, Calif., General Scanning of Watertown, Mass., Hewlett Packard of Palo Alto, Calif. and Hitachi USA of So. San Francisco, Calif. Analysis of the data, (i.e., collection, reconstruction of image, comparison and interpretation of data) is performed with associated computer systems and commercially available software, such as IMAGEQUANT™ by Molecular Dynamics. Moreover, the present invention does not require that optical interrogation be used to evaluate an assay. Advantageously, the present invention can use any interrogation or detection systems or methods.

Thus there has been described new systems, tools and methods of assaying biological materials. The array assays of the invention are advantageously addressable and self-assembling using the systems, tools and methods of the invention. Multiplexing of one or a plurality of the same or different samples and one or a plurality of the same or different targets per sample are possible on the single array apparatus with the systems, tools and methods of the invention. Good specificity and sensitivity of the systems and tools provide more accurate assay results. The assay tools are relatively inexpensive to make since the invention provides for generic or universal assay apparatuses with capture probes and separately provides custom solution probes. It should be understood that the above-described embodiments are merely illustrative of the some of the many specific embodiments that represent the principles of the present invention. Clearly, numerous other arrangements can be readily devised by those skilled in the art without departing from the scope of the present invention.

What is claimed is:

1. An assay system comprising:
    an apparatus having a plurality of first probes attached to a substrate, each of said first probes comprising a sequence of nucleotides having a first polarity and a first nucleotide having a second polarity; and
    a plurality of second probes, each of said second probes comprising a first region and a second region, wherein said first region is complementary to the first probe and comprises a sequence of nucleotides that has said first polarity and a second nucleotide having said second polarity, and wherein said second region binds to a biological material to be assayed;
    wherein said second polarity is reversed relative to said first polarity; and
    wherein said first nucleotide base pairs with said second nucleotide.

2. The assay system of claim 1, wherein the biological material to be assayed comprises a group selected from oligonucleotides, cDNAs, RNAs, PCR products, proteins, amino acids, antigens, antibodies, receptors, and ligands.

3. The assay system of claim 1, wherein the second region of the second probe comprises a group selected from oligonucleotides, cDNAs, RNAs, PCR products, proteins, amino acids, antigens, antibodies, receptors, and ligands that binds with the biological material to be assayed.

4. The assay system of claim 1, wherein the each first probe further comprises a first member of a specific binding pair, and the first region of each second probe comprises a second member of the specific binding pair, the first member and the second member cross-link.

5. The assay system of claim 1, wherein the first probes are located in an array of features on the substrate, at least some of the first probes being different from others in the plurality of first probes, a different first probe being located at a different feature address of the array, and
    wherein one or both of the first region and the second region of at least some of the second probes is different from respective other first regions and other second regions of the second probes, such that some of the second probes of the plurality are different from each other, a biological material to be assayed being addressable to a respective feature address on the array by a respective second probe according to the first region and the respective first probe.

6. An assay system comprising:
    an array apparatus that comprises a plurality of first probes on a substrate in an array of features, at least some first probes being different from others in the plurality of first probes, a different first probe being located at a different feature and being a different address on the array, wherein each of said at least some first probes comprises a first nucleotide with a reversed polarity relative to other nucleotides of said first probe; and
    a plurality of second probes, each second probe comprising a first region and a second region, one or both of the first region and the second region being different from respective other first regions and other second regions of at least some of the second probes, such that some of the second probes in the plurality of second probes are different, the first region of the second probe binding with a respective first probe,
    wherein the first region of at least some second probes comprises a second nucleotide with the same polarity as said reversed polarity of said first nucleotide; wherein said second nucleotide preferentially binds to the first nucleotide of the first probes instead of to a complementary nucleotide whose polarity has not been reversed, and
    wherein the second region of the second probes binds with a specific target of a biological material to be assayed to address the specific target to a feature address on the array corresponding to the respective first probe.

7. The assay system of claim 6, wherein the second region of at least some second probes is different from the second region of other second probes, the first region being the same on the at least some second probes, the different second regions binding with different portions of the specific target to address the different portions of the specific target to a same feature address on the array corresponding to the respective first probe.

8. The assay system of claim 7, wherein the specific target is addressable to the same feature address using different second probes.

9. The assay system of claim 6, wherein the second region of at least some second probes is different from the second region of other second probes, the first region being different on the second probes, the different second region binding with a different specific target, such that the different specific targets are addressable to different feature addresses on the array corresponding to the first region of the respective different second probes and the respective first probes.

10. The assay system of claim 6, wherein the second region of at least some second probes is the same and binds with a same specific target, the same specific target being in a plurality of different biological samples, the first region being different on the second probes, such that the different biological samples are distinguishable according to where the corresponding same specific target is addressed on the array by the first regions of the respective second probes and the respective first probes.

11. The assay system of claim 6, wherein the second region of at least some second probes is different and binds with a different specific target, the first region being different on the second probes, the different specific targets being in a plurality of different biological samples, such that each different specific target and each different sample are distinguishable according to where the different specific targets are addressed on the array by the different first regions of the respective different second probes and the respective different first probes.

* * * * *